United States Patent
Sipos et al.

(10) Patent No.: US 9,556,163 B2
(45) Date of Patent: Jan. 31, 2017

(54) PROCESS FOR THE PREPARATION OF A RIVAROXABAN AND INTERMEDIATES FORMED IN SAID PROCESS

(75) Inventors: Eva Sipos, Budapest (HU); Gyorgyi Kovanyine Lax, Budapest (HU); Balazs Havasi, Budapest (HU); Balazs Volk, Budapest (HU); Gyorgy Krasznai, Budapest (HU); Gyorgy Ruzsics, Budapest (HU); Jozsef Barkoczy, Budapest (HU); Maria Tothne Lauritz, Budapest (HU); Gyula Lukacs, Budapest (HU); Andras Boza, Budapest (HU); Laszlo Jozsef Hegedus, Maglod (HU); Maria Julia Taborine Toth, Tapioszecso (HU); Eva Pecsi, Budapest (HU)

(73) Assignee: EGIS Gyogyszergyar Nyilvanosan Mukodo Reszvenytarsasag, Budapest (HU)

( * ) Notice: Subject to any disclaimer, the term of this patent is extended or adjusted under 35 U.S.C. 154(b) by 176 days.

(21) Appl. No.: 14/115,359

(22) PCT Filed: May 4, 2012

(86) PCT No.: PCT/HU2012/000033
§ 371 (c)(1),
(2), (4) Date: Jan. 27, 2014

(87) PCT Pub. No.: WO2012/153155
PCT Pub. Date: Nov. 15, 2012

(65) Prior Publication Data
US 2014/0142303 A1    May 22, 2014

(30) Foreign Application Priority Data

May 6, 2011  (HU) .................................... 1100238
May 6, 2011  (HU) .................................... 1100239
May 6, 2011  (HU) .................................... 1100240

(51) Int. Cl.
*C07D 413/14*  (2006.01)
*C07D 303/36*  (2006.01)
*C07D 413/10*  (2006.01)
*C07D 265/32*  (2006.01)

(52) U.S. Cl.
CPC .......... *C07D 413/14* (2013.01); *C07D 265/32* (2013.01); *C07D 303/36* (2013.01); *C07D 413/10* (2013.01)

(58) Field of Classification Search
CPC .................................................. C07D 413/14
See application file for complete search history.

(56) References Cited

U.S. PATENT DOCUMENTS

| | | | |
|---|---|---|---|
| 6,417,403 B1 | 7/2002 | Roh et al. | |
| 6,833,453 B2 | 12/2004 | Perrault et al. | |
| 6,998,420 B2 | 2/2006 | Perrault et al. | |
| 7,767,702 B2 | 8/2010 | Straub et al. | |
| 7,816,355 B1 | 10/2010 | Bodhuri et al. | |
| 8,101,609 B2 | 1/2012 | Bodhuri et al. | |
| 8,106,192 B2 | 1/2012 | Thomas | |
| 8,178,525 B2 | 5/2012 | Song et al. | |
| 2002/0086900 A1 | 7/2002 | Perrault et al. | |
| 2004/0143131 A1 | 7/2004 | Perrault et al. | |
| 2004/0242660 A1 | 12/2004 | Straub et al. | |
| 2005/0215801 A1 | 9/2005 | Kitajima et al. | |
| 2007/0149522 A1 | 6/2007 | Thomas | |
| 2010/0081807 A1 | 4/2010 | Thomas | |
| 2010/0120718 A1* | 5/2010 | Perzborn ............ | A61K 31/4365 514/81 |
| 2010/0267685 A1 | 10/2010 | Straub et al. | |
| 2010/0273790 A1 | 10/2010 | Bodhuri et al. | |
| 2010/0273798 A1 | 10/2010 | Bodhuri et al. | |
| 2011/0112083 A1 | 5/2011 | Song et al. | |
| 2011/0275805 A1 | 11/2011 | Wang et al. | |

FOREIGN PATENT DOCUMENTS

| | | |
|---|---|---|
| CN | 102408420 A | 4/2012 |
| EP | 1553093 A1 | 7/2005 |
| EP | 2388251 A1 | 11/2011 |
| WO | 9952855 A1 | 10/1999 |
| WO | 0232857 A1 | 4/2002 |
| WO | 03000256 A1 | 1/2003 |
| WO | 2004060887 A1 | 7/2004 |
| WO | 2010002115 A2 | 1/2010 |
| WO | 2010081404 A1 | 7/2010 |
| WO | 2010124385 A1 | 11/2010 |

OTHER PUBLICATIONS

International Search Report from PCT/HU2012/000033 dated Oct. 16, 2012.

* cited by examiner

*Primary Examiner* — Rebecca Anderson
(74) *Attorney, Agent, or Firm* — Millen White Zelano and Branigan, PC; Csaba Henter; Anthony Zelano

(57) ABSTRACT

The invention relates to a process for the preparation of 5-chloro-N-({(5-S)-2-oxo3-[4-(3-oxo-morj)holine-4-yl)-phenyl]-1,3-oxazolidine-5-yl}-methyl) thiophen-2-carbox-amide having the INN rivaroxaban. The invention also relates to intermediates formed in the above process.

19 Claims, 6 Drawing Sheets

G = OR, NRR', or CX$_3$
R, R' = alkyl-, aryl-, aryl-alkyl-,
substituted alkyl- or aryl group
X = halogenic atom
L$^1$ = halogenic, C$_{1-4}$ alkoxy, imidazole, ester,
trihalomethoxy, N-hydroxy-succinimide
L$^2$= halogenic atom,
    alkyl- or arylsulfonyloxy-group

PROCESS FOR THE PREPARATION OF A RIVAROXABAN AND INTERMEDIATES FORMED IN SAID PROCESS

THE TECHNICAL FIELD OF THE INVENTION

The present invention is directed to a process for the preparation of a pharmaceutical active ingredient and intermediates formed in said process. More particularly the invention relates to a new process for the preparation of 5-chloro-N-({(5S)-2-oxo-3-[4-(3-oxo-morpholine-4-yl)-phenyl]-1,3-oxazolidine-5-yl}-methyl)-thiophen-2-carboxamide of the Formula

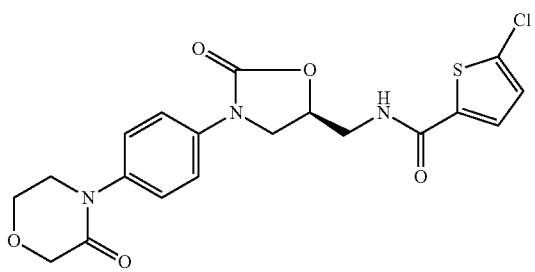

having the INN rivaroxaban. The invention is also directed to intermediates formed in said process.

THE STATE OF THE ART

It is known that 5-chloro-N-({(5S)-2-oxo-3-[4-(3-oxo-morpholine-4-yl)-phenyl]-1,3-oxazolidine-5-yl}-methyl)-thiophen-2-carboxamide having the INN rivaroxaban is a pharmaceutical active ingredient of a Xa coagulation factor inhibitor mechanism suitable for the treatment of deep venous thrombosis nyocardial infarction, angina pectoris, arterial occlusion, arterial restenosis and pulmonary embolism.

Rivaroxaban was first described by Straub et al in EP 1261606. In said European patent a broad group of substituted oxazolidines and a process for the preparation thereof was disclosed. Specifically neither the preparation of rivaroxaban nor the physico-chemical characteristics thereof were disclosed. The total yield of the synthesis was not set forth either. According to the general teaching of the patent the preparation of rivaroxaban of the Formula 1 is carried out as shown on reaction scheme 1. Thus the configuration corresponding to rivaroxaban is derived from (S)-glycidyl-phthalimide of the Formula

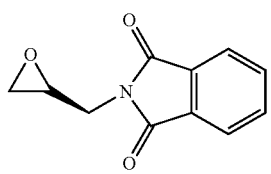

having the systematic chemical name 2-[(2S)-oxirane-2-yl-methyl]-1H-isoindole-1,3(2H)-dione which can be prepared from (S)-epichlorohydrine. In the last step of the synthesis according to the general procedures 4-{4-[(5S)-5-aminom-ethyl)-2-oxo-1,3-oxazolidine-3-yl]-phenyl-morpholine-3-on hydrochloride of the Formula

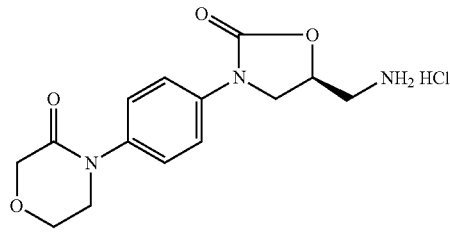

Is reacted with 5-chloro-thiophen-2-carboxylic acid chloride of the Formula

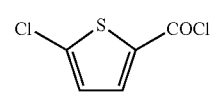

to yield rivaroxaban of the Formula 1. The coupling reaction is performed in pyridine. The drawback of the process is that the final coupling reaction is carried out by using the very expensive 5-chloro-thiophen-2-carboxylic acid chloride and using the highly toxic pyridine as solvent. A further disadvantage is that 5-chloro-thiophen-2-carboxylic acid chloride is a viscous oil difficult to handle. It easily decomposes and when stored at 0-5° C. quickly hydrolyses to 5-chloro-thiophen-2-carboxylic acid. Thus said starting material can not be stored but must be immediately used which makes the technology difficult, particularly on industrial scale production. 5-chloro-thiophen-2-carboxylic acid chloride is prepared from 5-chloro-thiophen-2-carboxylic acid with the aid of thionyl chloride: the latter reactant is also corrosive, has an unpleasant odor and is detrimental to health and the environment. At the end of the reaction the residual thionyl chloride is to be removed which necessitates a further distillation step. The hydrogen chloride and the sulphur dioxide by-products formed in course of the preparation of the acid chloride must be absorbed and handled which represents a further technological difficulty and causes health hazards.

In EP 1583761 an entirely different synthesis route is described which is shown on reaction scheme 2. Thus rivaroxaban of the Formula 1 is prepared by using as starting material (2S)-3-amino-propane-1,2-diol-hydrochloride salt. In said EP certain steps of the process and some intermediates are disclosed. The total yield of the process is only 37%. The 5-chloro-thiophen-2-carbonyl structural unit is introduced by using 5-chloro-thiophen-2-carboxylic acid chloride. The drawbacks thereof are discussed above.

In WO 2005/026135 the preparation of the intermediate-4-(4-amino-phenyl)-morpholine-3-on of the Formula

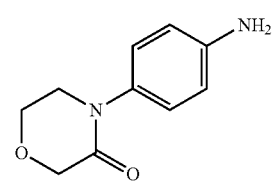

used in previously mentioned two patent applications is described, as shown on reaction scheme 3. In said international patent application the catalytic hydrogenation of 4-(4-nitro-phenyl)-3-morpholinone of the Formula

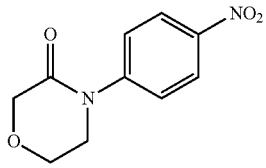

6 in an aliphatic alcohol is protected. Said process differs from the method set forth in EP 1261606 in that catalytic hydrogenation is carried out in tetrahydrofurane.

According to WO 2005/0068456 (equivalent to DE 102004002044) rivaroxaban is prepared by the synthesis route shown on reaction scheme 4. Said process is practically identical with the method disclosed in the basic patent and shown on reaction scheme 1 except that the yields of some steps were improved by optimization of the reaction conditions. In said international patent application the preparation of rivaroxaban by coupling 4-{4-[(5S)-5-aminomethyl-2-oxo-1,3-oxazolidine-3-yl]-phenyl}-morpholine-3-on hydrochloride of the Formula 3a with 5-chloro-thiophen-2-carboxylic acid chloride of the Formula 4 in an ether, alcohol or ketone type solvent or a mixture thereof in the presence of an inorganic base is described. As solvent for the coupling reaction preferably a mixture of acetone and water and as inorganic base preferably sodium hydroxide, sodium hydrogen carbonate or sodium carbonate, particularly sodium carbonate can be used. In the example showing the coupling step from the salt of the Formula 3a with sodium carbonate the base is in situ set free, whereupon water and acetone are added and the about 30 weight % solution of 5-chloro-thiophen-2-carboxylic acid chloride of the Formula 4 in toluene is added dropwise at 8-12° C. Thereafter at 50° C. acetone is added, the reaction is continued, the reaction mixture is cooled to 25° C. and rivaroxaban is filtered off. The disadvantages of the 5-chloro-thiophen-2-carboxylic acid chloride reactant used in said process were discussed above. A further drawback of the process resides in the fact that the removal of the phthalyl protecting group with a large excess (4.4 equiv.) of methyl amine is performed only in a late stage of the process. Since a large excess of methyl amine and severe reaction conditions are used, the formation of contaminations is inevitable. The yields show that said process is uneconomical.

WO 2005/068456 is silent in mentioning the HPLC purity of certain intermediates let alone that of the end product rivaroxaban of the Formula 1. The hydrochloride salt of the Formula 3a is obtained according to the international patent application with a yield of 82.7%, while there is no disclosure relating to the purity thereof. On reproducing the example of the above patent application we have found that complete removal of the protecting group requires at least 20 hours rather than 2 hours as taught by the international patent application. After removal of the phthalyl protecting group the quality of the intermediate of the Formula 3a is unsuitable for the preparation of a pharmaceutical grade end product. Therefore the intermediate of the Formula 3a must be subjected to recrystallization which decreases the overall yield of the process.

A publication published in IP.com. Journal in 2010 (IPCOM00000195906D) the preparation of 4-(4-amino-phenyl)-morpholine-3-on of the Formula 5 is dealt with starting from 4-(4-nitro-phenyl)-3-morpholinone of the Formula 6. In order to avoid catalyical hydrogenation the authors elaborated a new reduction method whereby reduction was carried out with a metal or metal salt in the presence of an acid. As metal preferably zinc or iron was used and as acid advantageously hydrochloric acid was applied: the reaction medium was alcohol or a mixture of alcohol and water. The best yield reported was 78%.

In the publication IP.com Journal published in IP.com Journal (IPCOM000190589D) in 2009 the I, II, III, IV crystalline forms of 4-{4-[(5S)-5-aminomethyl-2-oxo-1,3-oxazolidine-3-yl]-phenyl}-morpholine-3-one of the Formula

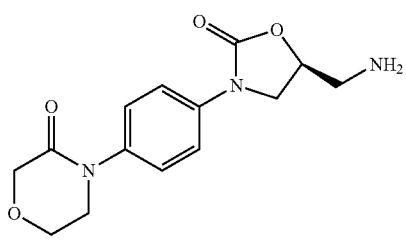

12 and the mesylate (A crystalline form), tartarate (B form), phosphate (C), citrate (D), sulfate (E), 5-chloro-thiophen-2-carboxylic acid salt (F), fumarate (G), tosylate (H), maleate (J) and hydrogen bromide (K) salts are described and characterized by XRD spectra.

In WO 2010/124385 new synthesis routes for the preparation of rivaroxaban and the enantiomer thereof are disclosed. These and the substitute definitions are shown on reaction scheme 5. The concrete examples for the preparation of rivaroxaban teach the reaction of the compound of the Formula

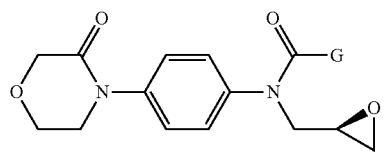

7 and 5-chloro-thiophen-2-carboxylic acid of the Formula

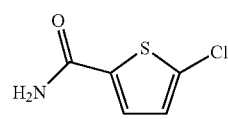

8

As base in the three examples butyl lithium (yield 62%), LiCl—Bu$^t$OK (yield 32) and LiHMDS (yield 64%) are used. The batch sizes are below 1 g. Thus it is uncertain whether this process is suitable for industrial scale production. The inventors purified the product in each step by means of chromatography and this process is unsuitable for scaling up the manufacturing process.

In the general reaction scheme of WO2010/124385 (reaction scheme 5) compounds of the Formula

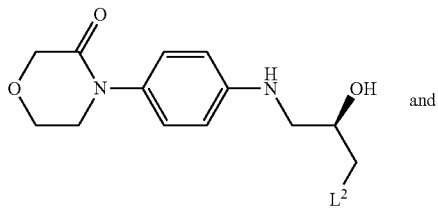
9

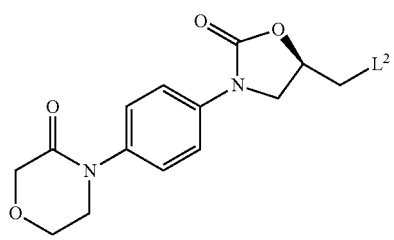
10 are disclosed wherein L² stands for halogen or an alkyl- or arylsulfonyloxy group. From the compound of the Formula 10 formally by reacting with 5-chloro-thiophen-2-carboxylic amide of the Formula 8 rivaroxaban of the Formula 1 can be prepared. Actually, in this application neither the preparation of the compounds of the Formulae 9 and 10 nor the physicochemical characteristics thereof were described. Thus the general reaction scheme mentions this reaction variant only as a theoretical possibility. This part of the patent application is further weakened by the experimental experience showing that the compound of the Formula

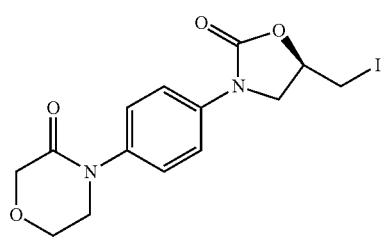
10c containing a very good leaving group (said compound is the compound of the Formula 10 in which L² stands for I) does not react with the amide of the Formula 8 by using an organic or inorganic base (KOBu$^t$, pyridine) under very severe conditions (90° C., DMF).

In WO 2011/012321 processes are disclosed for the purification of rivaroxaban by crystallization and for the preparation of high purity rivaroxaban. On reaction scheme 6 of the international patent application an example is presented for the preparation of the compound of the Formula 1 by reacting 5-chloro-thiophen-2-carboxylic acid of the Formula

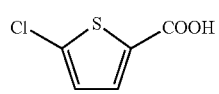
15 and N,N'-carbonyl-diimidazole (1.2 equiv.) and triethyl amine (1.2 equiv.) and the hydrochloric acid salt of the Formula 3a (1.03 equiv.) in dimethyl formamide. However according to this process crude rivaroxaban can be obtained only with high losses with a yield of 72% (related to the compound of the Formula 3a) and the crude product obtained requires further purification. The yield of the purified product is 61% (related to the compound of the Formula 3a) is only medium and is much lower than that of acylation reactions carried out with the acid chloride of the Formula 4 The patent application is silent in disclosing any data relating to the purity of the product.

BRIEF DESCRIPTION OF THE INVENTION

Figure 1:
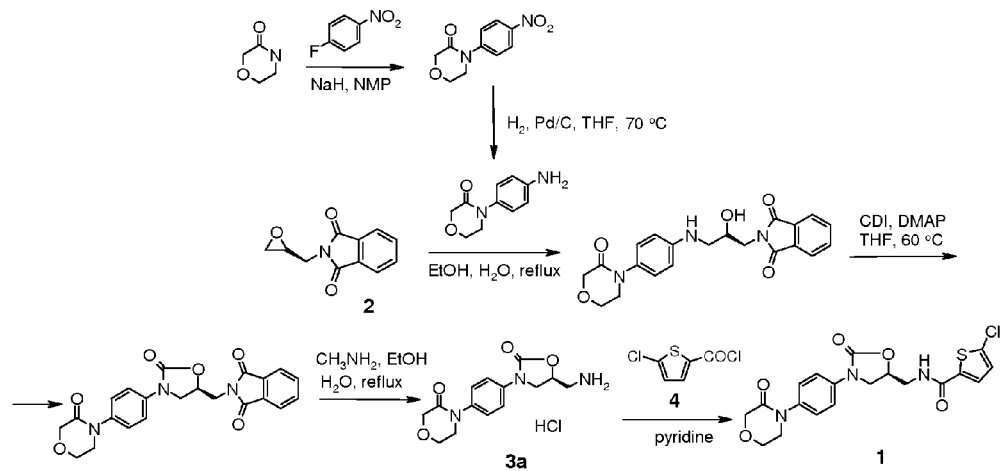
FIG. 1 Illustrates reaction scheme 1.
Figure 2:
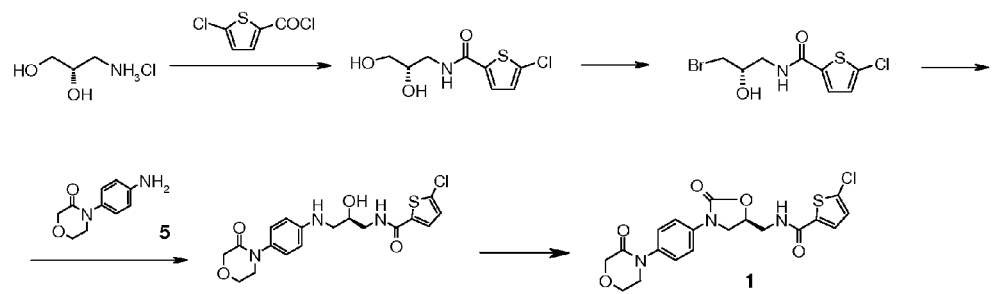
FIG. 2 Illustrates reaction scheme 2.
Figure 3:
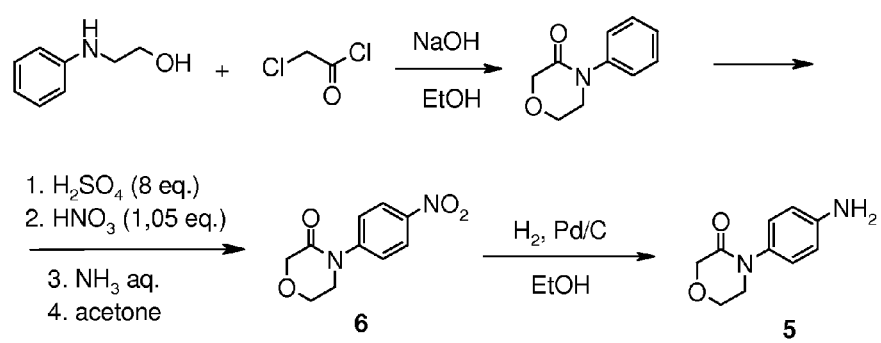
FIG. 3 Illustrates reaction scheme 3.
Figure 4:
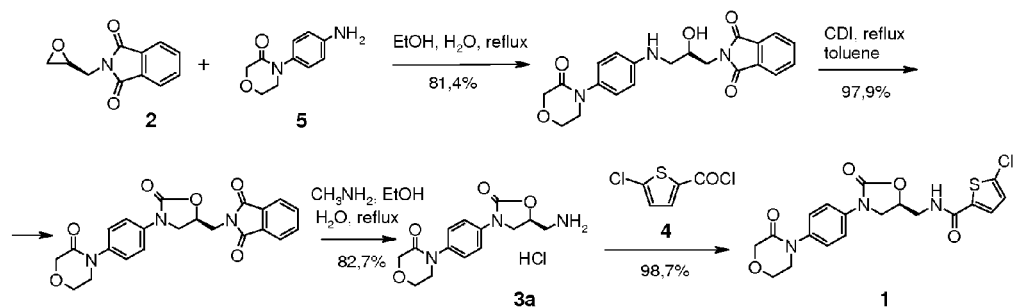
FIG. 4 Illustrates reaction scheme 4.
Figure 5:
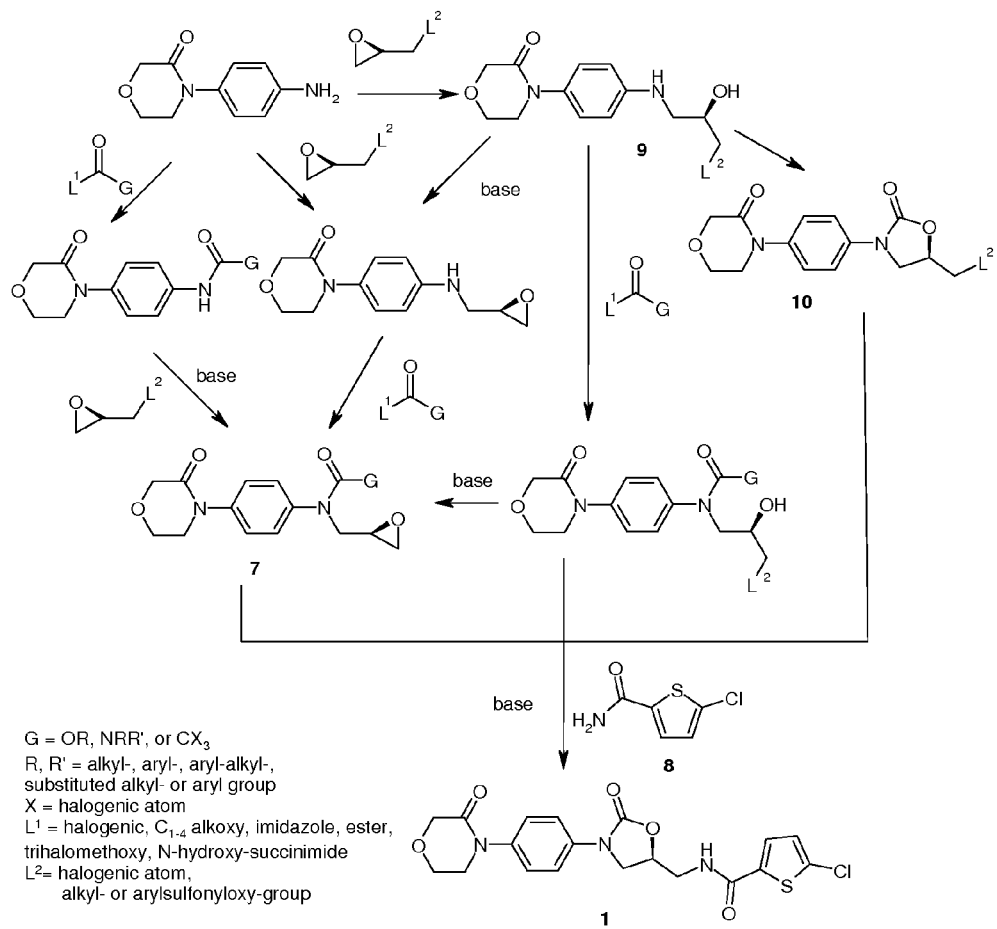
FIG. 5 Illustrates reaction scheme 5.
Figure 6:
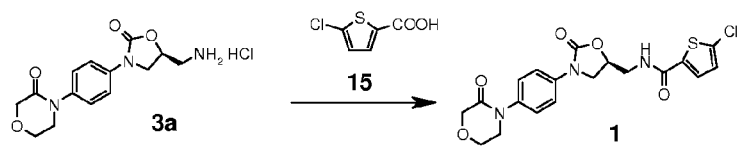
FIG. 6 Illustrates reaction scheme 6.
Figure 7A:
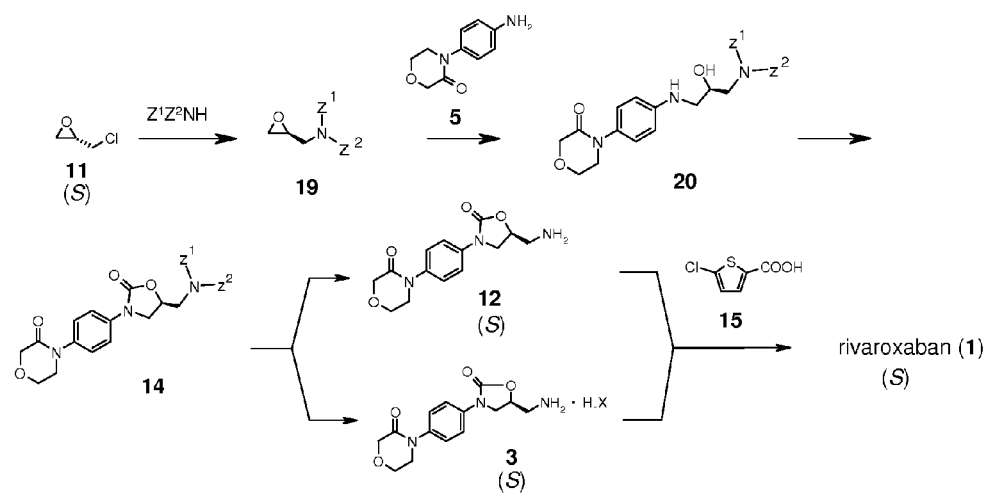
FIG. 7A Illustrates reaction scheme 7A.
Figure 7B:
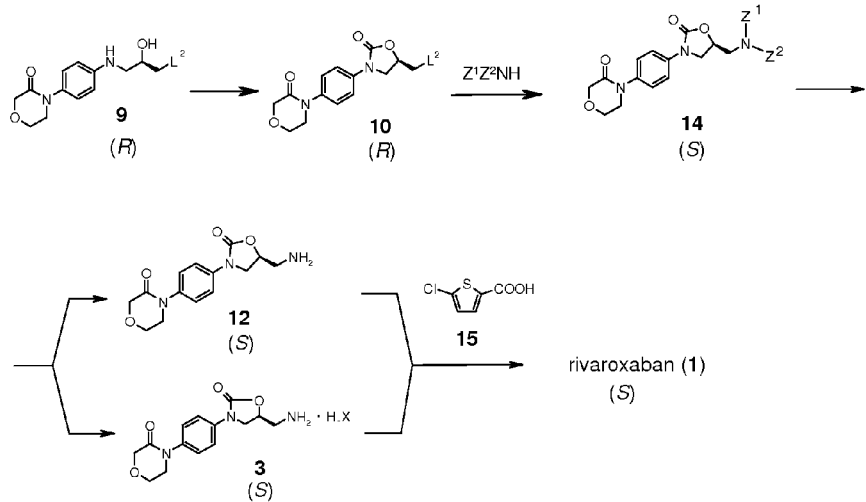
FIG. 7B Illustrates reaction scheme 7B.
Figure 8A:
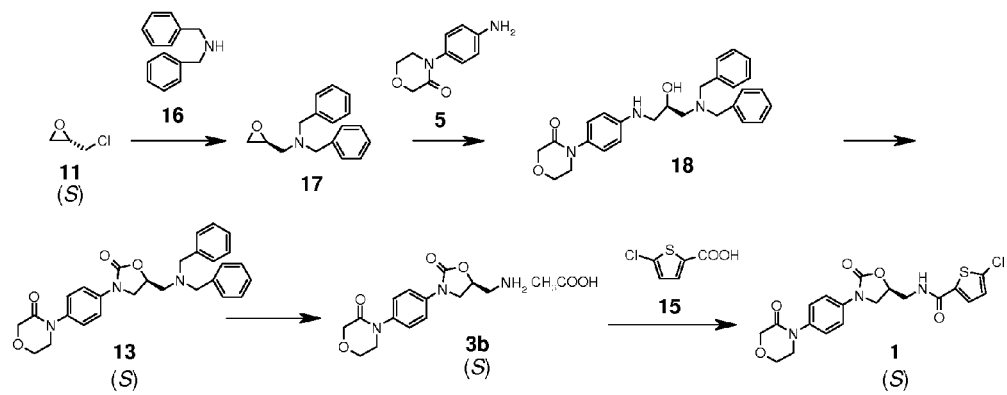
FIG. 8A Illustrates reaction scheme 8A.
Figure 8B:
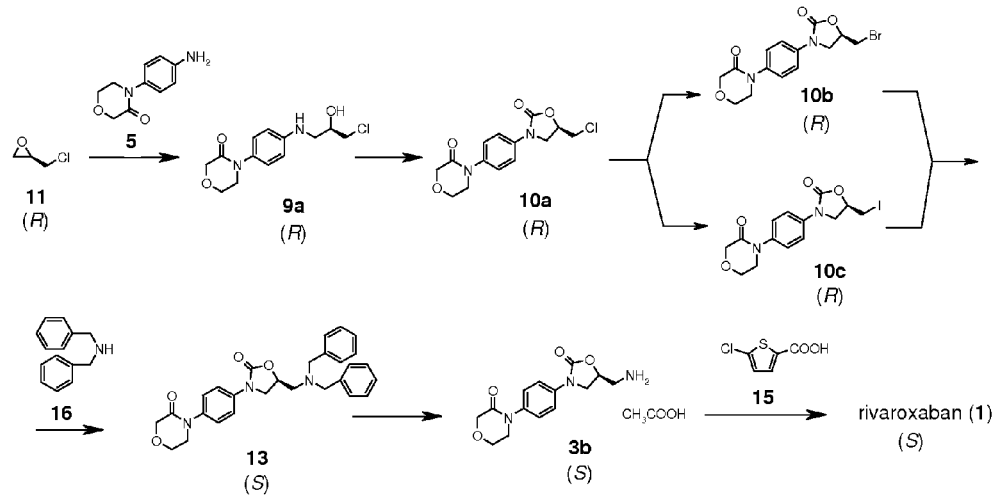
FIG. 8B Illustrates reaction scheme 8B.
Figure 9:
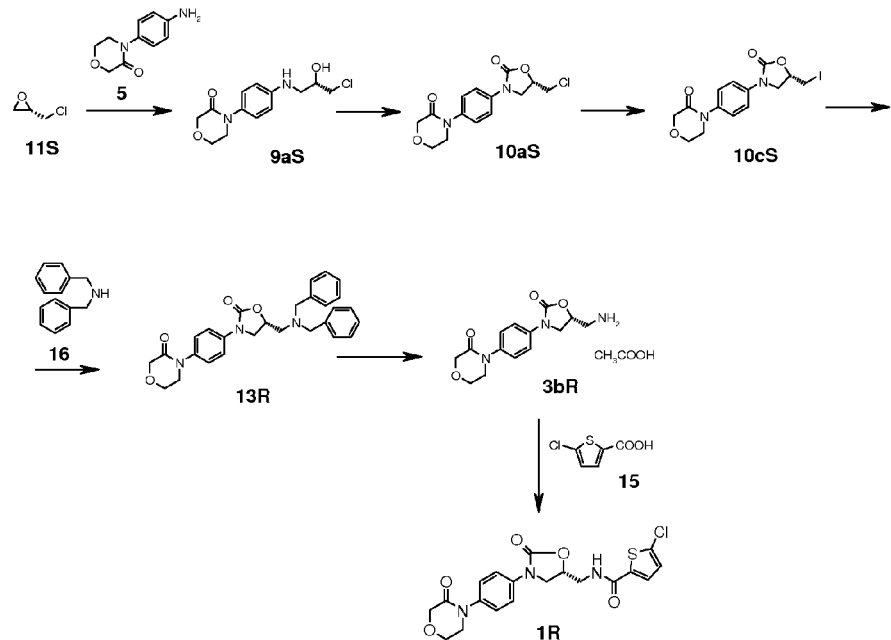
FIG. 9 Illustrates reaction scheme 9.
Figure 10:
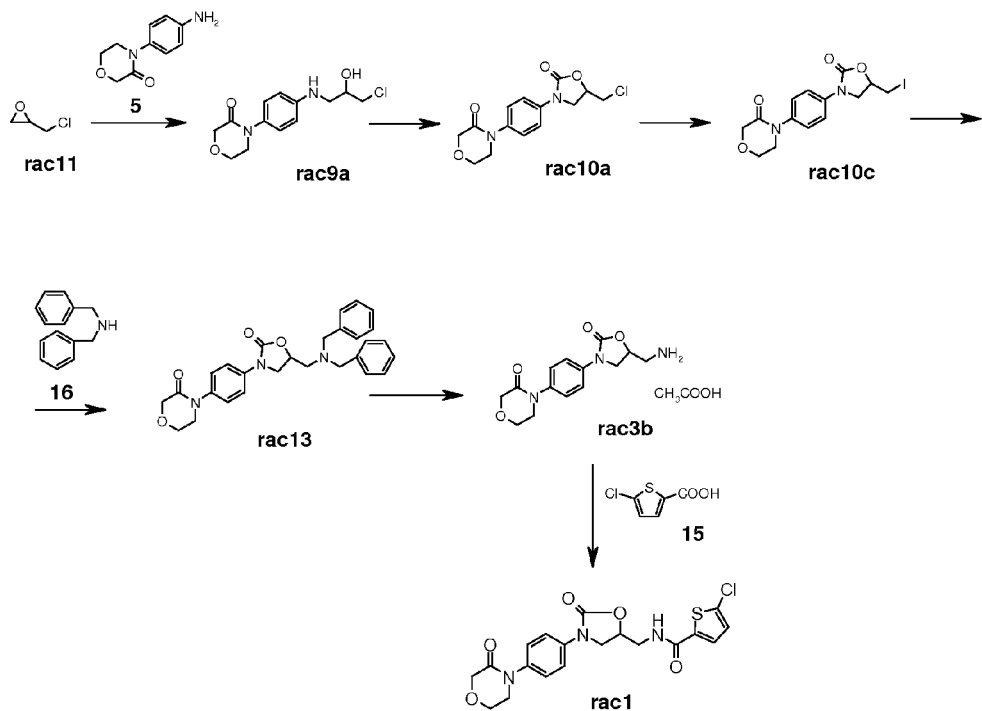
FIG. 10 Illustrates reaction scheme 10.

The object of the invention is to elaborate an industrial scale synthetic process for the preparation of rivaroxaban of the Formula 1 which process provides better yields and uses crystalline and easily purifiable intermediates.

The above object is achieved by means of the following process.

In the first step of the process a compound of the general Formula

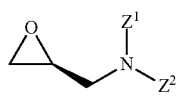
19

(wherein $Z^1$ and $Z^2$ stand for hydrogen or a conventional amino protecting group, e.g. benzyl, substituted benzyl, p-methoxy-benzyl, benzyloxycarbonyl or tert. butoxycarbonyl with the proviso that at least $Z^1$ is other than hydrogen and $Z^1$ and $Z^2$ are preferably benzyl/is prepared by reacting the compound of the Formula

11 with a compound of the general Formula $Z^1Z^2$NH.

In the second step of the process the compound of the general Formula 19 is reacted with the compound of the Formula 5 to yield a compound of the general Formula

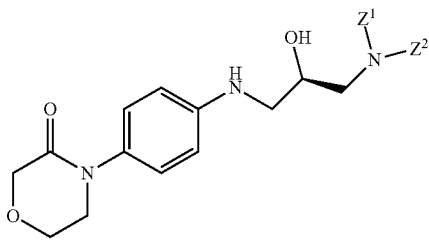

20

(wherein Z1 and Z² are as stated above).

In the third step of the process a compound of the general Formula

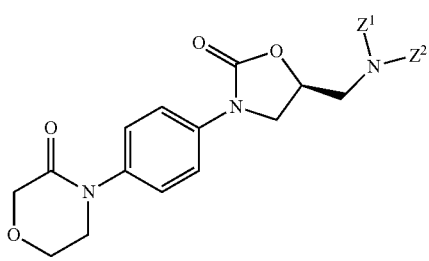

14

(wherein $Z^1$ and $Z^2$ are as stated above) is prepared by reacting a compound of the general Formula 20 with an agent capable of introducing the carbonyl group.

In the fourth step of the process from a compound of the general Formula 14 the base of the Formula 12 or a salt thereof of the general Formula

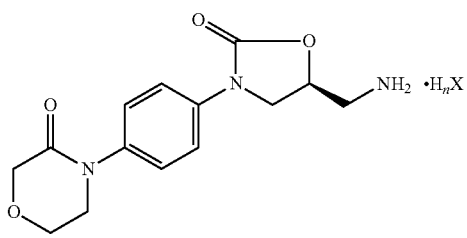

3

(wherein $H_nX$ is a mono- or bivalent organic or inorganic acid; n represents 1, 2 or 3 and X stands for an acid residue ion) is prepared by removing the protecting group(s). As organic acid e.g. a sulfonic acid, a carboxylic acid including monovalent carboxylic acids e.g. formic acid, acetic acid, propionic acid, butyric acid etc. and as inorganic acids e.g. sulfuric acid, sulfurous acid, nitric acid, phosphoric acid, hydrogen bromide, hydrogen iodide can be used.

In the last step of the process the base of the Formula 12 or a salt thereof of the general Formula 3 (wherein $H_nX$ is as stated above) is reacted with 5-chloro-thiophen-2-carboxylic acid to yield rivaroxaban of the Formula 1. In the last acylation step of the preparation of rivaroxaban we use the acid of the Formula 15 which is considerably less reactive than 5-chloro-thiophen-2-carboxylic acid chloride of the Formula 4 previously applied in the last acylation step of the preparation of rivaroxaban of the Formula 1. Said reaction is carried out in the presence of a coupling agent and an organic or inorganic base, in an inert solvent: if desired the use of the acid binding agent can be omitted. The process can be carried out by using a racemic starting material, if desired. In this case at first the compounds having a chirality shown on reaction schema 7a, 7b, 8a and 8b are prepared by resolution.

The compounds of the general Formula 14 can be surprisingly also prepared in a manner that in the first step from a compound of the general Formula 9 by reacting with an agent capable of introducing a carbonyl group a compound of the general Formula 10 is prepared (wherein $L^2$ stands for chlorine, bromine, iodine, alkylsulfonyloxy or arylsulfonyloxy, e.g. methanesulfonyloxy, benzenesulfonyloxy or p-toluenesulfonyloxy, preferably chlorine, bromine or iodine).

In the second step of the process a compound of the general Formula 10 (wherein $L^2$ has the same meaning as stated above) is reacted with a compound of the general Formula $Z^1Z^2NH$ (wherein $Z^1$ and $Z^2$ are hydrogen or a conventional amino protecting group, e.g. benzyl, substituted benzyl, p-methoxy-benzyl, benzyloxycarbonyl or tert. butoxycarbonyl with the proviso that at least one of symbols $Z^1$ and $Z^2$ is other than hydrogen, and $Z^1$ and $Z^2$ preferably stand for benzyl).

The invention also relates to intermediates used in the above process corresponding to the indicated general Formulae and to intermediates formed in the preferable embodiments of the above process.

DETAILED DESCRIPTION OF THE INVENTION

The invention relates to a process for the preparation of 5-chloro-N-({(5S)-2-oxo-3-[4-(3-oxo-morpholine-4-yl)-phenyl]-1,3-oxazolidine-5-yl}-methyl)-thiophen-2-carboxamide pharmaceutical active ingredient of the Formula 1 which comprises subjecting 4-{4-[(5S)-5-(aminomethyl)-2-oxo-1,3-oxazolidine-3-yl]-phenyl}-morpholine-3-one of the Formula 12 or the rac 12 Formula racemate thereof or a S-enantiomeric salt of the Formula 3 thereof or a racemate of the general Formula rac3 thereof (wherein HnX is a mono- or polyvalent organic or inorganic acid: n represents 1, 2 or 3: X stands for an acid residue ion) to resolution, if a racemic starting material is used, thereafter reacting with 5-chloro-thiophen-2-carboxylic acid of the Formula 15 in the presence of a coupling agent; or in the first step subjecting a S-enantiomeric compound of the general Formula 14 or a racemate thereof (wherein $Z^1$ and $Z^2$ stand for hydrogen or a protecting group with the proviso that at least $Z^1$ is other than hydrogen) to resolution, if a racemic starting material is used, thereafter removing the protecting group(s), and isolating the S-enantiomeric base of the Formula 12 thus obtained or a racemate or optionally a salt thereof; in the second step subjecting the product obtained to resolution, if a racemic starting material is used, and thereafter reacting with 5-chloro-thiophen-2-carboxylic acid of the Formula 15 in the presence of a coupling agent; or in the first step subjecting a R-enantiomeric compound of the general Formula 20 or a racemate thereof (wherein $Z^1$ and $Z^2$ are as stated above) to resolution, if a racemic starting material is used, thereafter reacting with an agent capable of introducing a carbonyl group thereafter reacting with an agent capable of introducing a carbonyl group; in the second step subjecting a S-enantiomeric compound of the general Formula 14 obtained or a racemate thereof to resolution, if a racemic starting material is used, thereafter reducing the product, separating the S-enantiomeric base of the Formula 12 thus obtained or a racemate thereof; in the third step subjecting the product obtained to resolution, if a racemic starting material is used, thereafter reacting with 5-chloro-thiophen-2-carboxylic acid of the Formula 15 in the presence of a coupling agent; or
in the first step subjecting an R-enantiomeric compound of the general Formula 19 or a racemate thereof (wherein $Z^1$ and $Z^2$ are as stated above) to resolution, if a racemic starting material is used, thereafter reacting with a 4-(4-aminophenyl)-morpholine-3-one compound of the Formula 5, in the second step subjecting the R-enantiomeric compound of the general Formula 20 or a racemate thereof (wherein $Z^1$ and $Z^2$ are as stated above) to resolution, if a racemic starting material is used, thereafter reacting with an agent capable of introducing a carbonyl group, in the third step subjecting the S-enantiomeric compound of the general Formula 14 obtained or a racemate thereof (wherein $Z^1$ and $Z^2$ are as stated above) to resolution, if a racemic starting material is used, removing the protecting group(s) and isolating the S-enantiomeric base of the Formula 12 thus obtained or a racemate or optionally a salt thereof; in the fourth step subjecting the product thus obtained to resolution, if a racemic starting material is used, and thereafter reacting with the 5-chloro-thiophen-2-carboxylic acid of the Formula 15 in the presence of a coupling agent; or
in the first step reacting a S-enantiomeric compound of the Formula 11 or the racemate thereof, with a compound of the general Formula $Z^1Z^2$NH (wherein $Z^1$ and $Z^2$ are as stated above) 1, in the second step subjecting a compound of the general Formula 19 thus obtained or the racemate thereof (wherein $Z^1$ and $Z^2$ are as stated above) to resolution, if a racemic starting material is used, thereafter reacting with the 4-(4-amino-phenyl)-morpholine-3-one of the Formula 5, in the third step subjecting a R-enantiomeric compound of the general Formula 20 obtained or the racemate thereof (wherein $Z^1$ and $Z^2$ are as stated above) to resolution, if a racemic starting material is used, thereafter reacting with an agent capable of introducing a carbonyl group; in the fourth step subjecting the S-enantiomeric compound of the general Formula 14 or the racemate thereof (wherein $Z^1$ and $Z^2$ are as stated above) to resolution, if a racemic starting material is used, thereafter removing the protecting group(s) and isolating the S-enantiomeric base of the Formula 12 thus obtained or the racemate or optionally a salt thereof, in the fifth step subjecting the product obtained to resolution, if a racemic starting material is used, thereafter reacting with 5-chloro-thiophen-2-carboxylic acid of the Formula 15 in the presence of a coupling agent; or
in the first step subjecting a R-enantiomeric compound of the general Formula 9 or the racemate thereof (wherein $L^2$ is as stated above) to resolution, if a racemic starting material is used, thereafter reacting with an agent capable of introducing a carbonyl group, converting a R-enantiomeric compound of the general Formula 10 obtained or the racemate thereof (wherein $L^2$ is as stated above), if desired the R-enantiomeric compound of the Formula

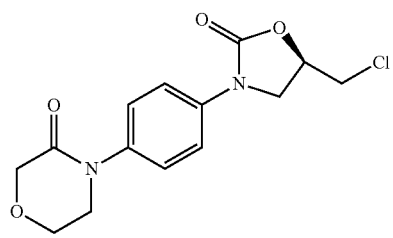

10a (wherein $L^2$ is chlorine or bromine) or the racemate thereof into the R-enantiomeric compound of the Formula

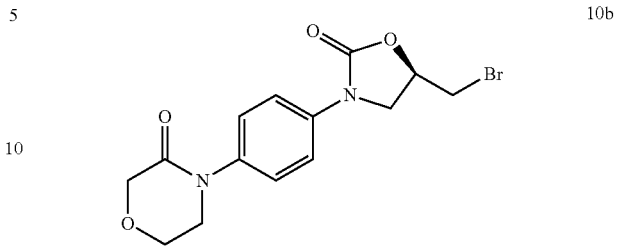

10b or a racemate thereof, or into a R-enantiomeric compound of the Formula 10c or the racemate thereof,
in the second step subjecting the R-enantiomeric compound of the general Formula 10 or the racemate thereof (wherein $L^2$ has the same meaning as stated above) to resolution, if a racemic starting material is used, thereafter reacting with a compound of the general Formula $Z^1Z^2$NH, in the third step subjecting a S-enantiomeric compound of the general Formula 14 or the racemate thereof (wherein $Z^1$ and $Z^2$ are as stated above) to resolution, if a racemic starting material is used, thereafter removing the protecting group(s) and isolating the S-enantiomeric base of the Formula 12 thus obtained or optionally a salt thereof;
in the fourth step subjecting the product thus obtained to resolution, if a racemic starting material is used, and reacting the product with 5-chloro-thiophen-2-carboxylic acid of the Formula 15 in the presence of a coupling agent,
with the proviso that if in the general Formula 3 n represents 1 and X stands for chlorine, then the coupling agent is other than N,N'-carbonyl-diimidazole.

According to a preferred embodiment of the invention n represents 1 and X stands for an acetate ion.

According to a preferred embodiment of the invention in the general Formula 14 $Z^1$ and $Z^2$ stand for benzyl.

According to a preferred embodiment of the invention in the general Formula 20 $Z^1$ and $Z^2$ stand for benzyl.

According to a preferred feature of the invention in the general Formula 19 $Z^1$ and $Z^2$ stand for benzyl.

According to a preferred feature of the invention in the general Formula $Z^1Z^2$NH $Z^1$ and $Z^2$ stand for benzyl.

According to a preferred embodiment of the invention the S-enantiomeric base of the Formula 12 or the racemate thereof or optionally a salt thereof is reacted with 5-chloro-thiophen-2-carboxylic acid of the Formula 15 in the presence of a chloro formiate, N,N'-diisopropyl-carbodiimide (DIC), N,N'-dicyclohexyl-carbodiimide (DCC), tripropyl phosphonic acid anhydride (T3P) or N,N'-carbonyl-diimidazole (CDI), preferably chloro ethyl formiate or CDI as coupling agent. The reaction is carried out preferably in the presence of an organic or inorganic base, advantageously triethyl amine, diisopropyl ethyl amine, sodium carbonate or sodium hydrogen carbonate, in an organic solvent, preferably acetonitrile, dichloro methane, acetone, toluene, tetrahydrofurane and mixtures thereof or mixtures of said solvents formed with water. The reaction is performed at a temperature of 0-110° C., preferably 40-70° C.

According to a further preferred embodiment of the invention the protecting group(s) of the S-enantiomeric compound of the Formula

13

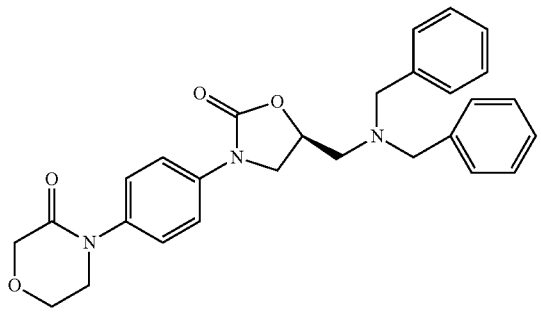

is (are) removed by reduction and said reduction reaction is carried out in a C1-4 aliphatic alcohol, glacial acetic acid, water or a mixture of said solvents formed with each other or other organic solvents. Catalytic hydrogenation or chemical reduction can be used.

According to further preferred embodiment of the present invention a R-enantiomeric compound of the general Formula 20 or a racemate thereof is converted into a S-enantiomeric compound of the general Formula 14 or a racemate thereof (wherein $Z^1$ and $Z^2$ are hydrogen or a protecting group with the proviso that at least $Z^1$ is other than hydrogen) by using as agent capable of introducing a carbonyl group N,N'-carbonyl-diimiazole, phosgene, diphosgene or triphosgene, advantageously N,N'-carbonyl-diimidazole. The reaction is carried out in a suitable solvent, preferably toluene.

According to a further preferred embodiment of the process the reaction of a R-enantiomeric compound of the Formula 19 or racemate thereof (wherein $Z^1$ and $Z^2$ are hydrogen or protecting group with the proviso that at least $Z^1$ is other than hydrogen) and the 4-(4-amino-phenyl)-morpholine-3-one of the Formula 5 is carried out preferably in a mixture of a protic solvent and water, at a temperature of 0-150° C., preferably at 60-90° C., preferably for a period of 20-40 hours, According to a further preferred embodiment of the invention the S-enantiomeric compound of the formula 11 is reacted with a compound of the general Formula $Z^1Z^2NH$ (wherein $Z^1$ and $Z^2$ are hydrogen or a protecting group with the proviso that at least $Z^1$ is other than hydrogen), preferably the reaction with N-benzyl-1-phenyl-methaneamine of the Formula

16

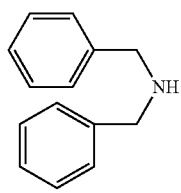

is performed in the absence of a solvent or in an organic solvent or water or a mixture thereof, preferably in the presence of an organic or inorganic acid binding agent.

According to a preferred embodiment of the invention the conversion of the R-enantiomeric compound of the Formula 10a or the racemate thereof into the R-enantiomeric compound of the Formula 10b or racemate thereof is carried out by reacting with an alkali bromide, preferably sodium bromide. The conversion into the compound of the Formula 10c of a racemate thereof is carried out by reacting with an alkali iodide, preferably sodium iodide and said reaction is carried out in a suitable organic solvent or a mixture thereof formed with water at 0-150° C., preferably at 80-130° C.

According to a further preferred embodiment of the invention the reaction with a compound of the general Formula $Z^1Z^2NH$ (wherein $Z^1$ and $Z^2$ stand for hydrogen or a protecting group with the proviso that at least $Z^1$ is other than hydrogen)—preferably with the N-benzyl-1-phenyl-methaneamine of the Formula 16) is carried out in the presence or absence of a solvent, in the presence of an organic or inorganic acid binding agent, preferably cesium carbonate at 0-150° C., preferably at 60-100° C.

According to a further preferred embodiment of the invention a R-enantiomeric compound of the general Formula 9 or a racemate thereof is converted into a R-enantiomeric compound of the general Formula 10 or a racemate thereof by using as agent suitable for the introduction of the carbonyl group N,N'-carbonyl-diimidazole, phosgene, diphosgene or triphosgene, preferably N,N'-carbonyl-diimidazole. The reaction is carried out in a solvent or solvent mixture, preferably toluene, 1.-methyl-2-pyrrolidone or a mixture thereof, at 0-150° C., preferably at the reflux temperature of the solvent or solvent mixture.

The invention also relates to 4-{4-[(5S)-5-(aminomethyl)-2-oxo-1,3-oxazolidine-3-yl]-phenyl}-morpholine-3-one and racemate thereof of the Formula 12, and S-enantiomeric salts of the general Formula 3 thereof and racemic salts of same (wherein HnX is a mono- or polyvalent organic or inorganic acid, n represents 1, 2 or 3 and X stands for an acid residue ion with the proviso that if n represents 1, then X is other than chlorine).

The invention also relates to the acetic acid salt of 4-{4-[(5S)-5-(aminomethyl)-2-oxo-1,3-oxazolidine-3-yl]-phenyl}-morpholine-3-one of the Formula

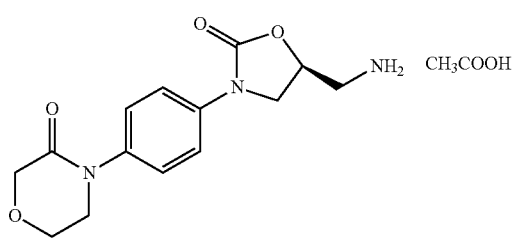

and the racemate thereof.

The invention also relates to a process for the preparation of the S-enantiomeric compound of the Formula 12 and the racemate thereof, or the S-enantiomeric salt of the general Formula 3 or a racemic salt thereof, preferably the acetic acid salt of the Formula 3b or racemic acetic acid salt thereof which comprises subjecting the S-enantiomeric compound of the general Formula 14 or a racemate thereof (wherein $Z^1$ and $Z^2$ stand for hydrogen or a protecting group with the proviso that at least $Z^1$ is other than hydrogen) to resolution, if a racemic starting material is used, preferably the S-enantiomeric compound of the Formula 13 or a racemate thereof (in this case $Z^1$ and $Z^2$ are benzyl) to resolution, if a racemic starting material is used, thereafter removing the protecting group 6(s) and isolating the S-enantiomeric base of the Formula 12 or the racemate thereof, or optionally a S-enantiomeric salt of the general Formula 3 or racemic salt thereof, preferably the acetic acid salt of the Formula 3b or the racemic acetic acid salt.

According to the invention there are also provided S-enantiomeric compounds of the general Formula 14 and racemates thereof (wherein $Z^1$ and $Z^2$ stand for hydrogen or a protecting group with the proviso that at least $Z^1$ is other than hydrogen and $Z^1$ and $Z^2$ together represent a group other than phthalimido).

The invention also relates to 4-(4-{(5S)-5-[(dibenzy-lamino)-methyl]-2-oxo-1,3-oxazolidine-3-yl}-phenyl)-morpholine 3-one of the Formula 13 and the racemate thereof.

According to the invention there is also provided a process for the preparation of S-enantiomeric compounds of the general Formula 14 and racemates thereof (wherein $Z^1$ and $Z^2$ stand for hydrogen or a protecting group with the proviso that at least $Z^1$ is other than hydrogen and $Z^1$ and $Z^2$ preferably stand for benzyl) which comprises subjecting a compound of the general Formula 20 (wherein $Z^1$ and $Z^2$ are as stated above) to resolution, if a racemic starting material is used, and thereafter reacting with an agent capable of introducing a carbonyl group.

The invention also relates to R-enantiomeric compounds of the general Formula 20 and racemates thereof (wherein $Z^1$ and $Z^2$ stand for hydrogen or a protecting group with the proviso that at least $Z^1$ is other than hydrogen and $Z^1$ and $Z^2$ together can not represent phthalimido).

The invention also relates to 4-(4-{[(2R)-33-(dibenzy-lamino)-2-hydroxypropyl]-amino}-phenyl)-morpholine-3-one of the Formula

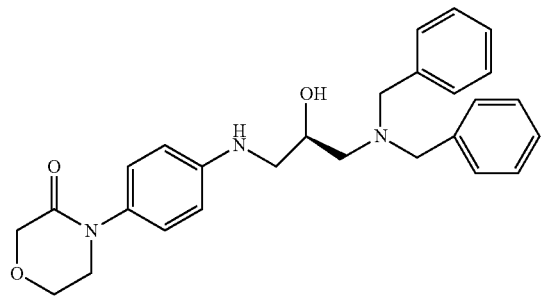

18

The invention also relates to a process for the preparation of R-enantiomeric compounds of the general Formula 20 and racemates thereof (wherein $Z^1$ and $Z^2$ stand for hydrogen or a protecting group with the proviso that at least $Z^1$ is other than hydrogen and preferably $Z^1$ and $Z^2$ are benzyl) which comprises subjecting a S-enantiomeric compound of the general Formula 19 or a racemate thereof (wherein $Z^1$ and $Z^2$ are as stated above) to resolution, if a racemic starting material is used, and thereafter reacting with 4-(4-amino-phenyl)-morpholine-3-one of Formula 5.

The invention also relates to S-enantiomeric compounds of the general Formula 19 and racemates thereof (wherein $Z^1$ and $Z^2$ stand for hydrogen or a protecting group with the proviso that at least $Z^1$ is other than hydrogen and if $Z^1$ stands for benzyl, $Z^2$ is other than benzyl).

The invention also relates to the preparation of S-enantiomeric compounds of the general Formula 14 and racemates thereof (wherein $Z^1$ and $Z^2$ stand for hydrogen or a protecting group with the proviso that at least $Z^1$ is other than hydrogen and $Z^1$ and $Z^2$ preferably stand for benzyl) which comprises subjecting a R-enantiomeric compound of the general Formula 10 or a racemate thereof (wherein $L^2$ stands for chlorine, bromine, iodine, alkylsulfonyloxy or arylsulfonyloxy(to resolution, if a racemic starting material is used, and thereafter reacting the product with a compound of the general Formula $Z^1Z^2NH$ (wherein $Z^1$ and $Z^2$ are as stated above).

The invention also relates to R-enantiomeric compounds of the general Formula 10 and racemates thereof (wherein $L^2$ is chlorine, bromine, iodine, alkylsulfonyloxy or arylsulfonyloxy, preferably chlorine, bromine or iodine).

The invention also relates to a process for the preparation of the R-enantiomeric compounds of the Formula 10 and racemates thereof wherein $L^2$ is chlorine, bromine, iodine, alkylsulfonyloxy or arylsulfonyloxy, preferably chlorine, bromine or iodine which comprises subjecting a R-enantiomeric compound of the Formula 9 (wherein $L^2$ as stated above) or a racemate thereof to resolution, if a racemic starting material is used, and thereafter reacting with an agent capable of introducing a carbonyl group/wherein $L^2$ is as stated above/.

The invention also relates to a process for the preparation of the R-enantiomeric compound of the Formula 10b or racemate of the Formula rac10b thereof or the R-enantiomeric compound of the Formula 10c or the racemate of the Formula rac10c thereof which comprises reacting the R-enantiomeric compound of the Formula 10a or the racemate of the Formula rac10a thereof with an alkali bromide, preferably sodium bromide or an alkali iodide preferably sodium iodide.

The invention also relates to R-enantiomeric compounds of the general Formula 9 and racemates thereof wherein $L^2$ is chlorine, bromine, iodine, alkylsulfonyloxy or arylsulfonyloxy, preferably chlorine, bromine or iodine.

The most general forms of realization of the synthesis of rivaroxaban of the Formula 1 are shown on reaction schema 7a and 7b.

The definitions in the Formulae in the reaction scheme 7a and 7b are as follows:

in the general Formulae $Z^1Z^2NH$, 19, 20 and 14 $Z^1$ and $Z^2$ are hydrogen or a protecting group, namely a conventional amino protecting group, e.g. benzyl, substituted benzyl p-methoxy-benzyl, benzyloxycarbonyl or tert. butoxycarbonyl with the proviso that at least $Z^1$ is other than hydrogen, and $Z^1$ and $Z^2$ preferably represent benzyl;

in the general Formula 3 HnX stands for a mono- or bivalent organic or inorganic acid (wherein n represents 1, 2 or 3 and X is an acid residue ion). As organic acid e.g. sulfonic acids and carboxylic acids, preferably monovalent carboxylic acids, e.g. formic acid, acetic acid, propionic acid, butyric acid and as inorganic acids e.g. sulfuric acid, sulfous acid, nitric acid, phosphoric acid, hydrochloric acid, hydrogen bromide, or hydrogen iodide may be used;

in the general Formulae 9 and 10 wherein $L^2$ is chlorine, bromine, iodine, alkylsulfonyloxy or arylsulfonyloxy, e.g. methanesulfonyloxy, benzenesulfonyloxy or p-toluenesulfonyloxy, preferably chlorine, bromine or iodine.

In the first step of the reaction route shown on reaction scheme 7a the compound of the Formula 11 is reacted with a compound of the general Formula $Z^1Z^2NH$ (wherein $Z^1$ and $Z^2$ are as stated above) in the absence of a solvent or in an organic solvent or water or a mixture thereof, preferably in the presence of an organic or inorganic acid binding agent.

In the second step of the reaction route shown on reaction scheme 7a a compound of the general Formula 19 (wherein $Z^1$ and $Z^2$ are as stated above) is reacted with the compound of the Formula 5. The reaction is carried out preferably in a protic solvent or solvent mixture or in a mixture of a protic solvent and water, at 0-150° C., preferably 60-90° C., for a period of 0.5-60 hours, preferably 20-40 hours.

In the third step of the reaction route shown on reaction scheme 7a from the compound of the general Formula 20 obtained a compound of the general Formula 14 is prepared (wherein $Z^1$ and $Z^2$ are as stated above). The reaction is carried out by using an agent capable of introducing a carbonyl group, preferably N,N'-carbonyl-diimidazole, phosgene, diphosgene or triphosgene, preferably N,N'-carbonyl-diimidazole, in a suitable solvent or solvent mixture, preferably toluene.

In the fourth step of the reaction route shown on reaction scheme 7a from a compound of the general Formula 14 (wherein $Z^1$ and $Z^2$ are as stated above) the base of the Formula 12 or a salt of the general Formula 3 thereof is prepared by removing the protecting group, preferably by means of reduction (wherein HnX is as stated above). Reduction is carried out in a C1-4 aliphatic alcohol, glacial acetic acid, water or a mixture of said solvents with each other or a further organic solvent. Catalytic hydrogenation or chemical reduction can be used.

The compound of the Formula 3b is directly isolated, or from the acetic acid salt of the Formula 3b the base of the Formula 12 is set free in a known manner or optionally the acetic acid salt obtained is converted into a salt of the general Formula 3 in a known manner (wherein HnX is as stated above).

In the last step of the reaction route shown on reaction scheme 7a the base of the Formula 12 or a salt of the general Formula 3 thereof (wherein HnX is as stated above (is reacted with 5-chloro-thiophen-2-carboxylic acid of the Formula 15 in the presence of a coupling agent and an organic or inorganic base in an organic solvent. As coupling agent a chloro formiate, N,N'-diisopropyl-carbodiimide (DIC), N,N'-dicyclohexyl-carbodiimide (DCC), tripropyl-phosphonic acid anhydride (T3P) or N,N'-carbonyl-diimidazole, preferably chloro ethyl formiate or CDI can be used. As solvent acetonitrile, dichloro methane, acetone, toluene, tetrahydrofurane or a mixture formed with each other or with water can be applied. As organic or inorganic base triethyl amine, diisopropyl ethyl amine, sodium carbonate or sodium hydrogen carbonate can be used. The reaction is carried out at 0-100° C., preferably at 40-70° C. The use of the acid binding agent can be optionally omitted.

In the first step of the reaction route shown on reaction scheme 7b from a compound of the general Formula 9 a compound of the general Formula 10 is prepared (wherein $L^2$ has the same meaning as stated above). In the reaction as agent capable of introducing the carbonyl group preferably N,N'-carbonyl-diimidazole, phosgene, diphosgene or triphosgene, particularly N,N'-carbonyl-diimidazole can be used. The reaction is carried out in a suitable solvent or solvent mixture, preferably toluene, 1-methyl-2-pyrrolidone or a mixture thereof, at 0-150° C., preferably at the reflux temperature of the solvent or solvent mixture.

If in the compounds of the general Formula 9 shown on reaction scheme 7b $L^2$ stands for chlorine i.e. the compound is of the Formula

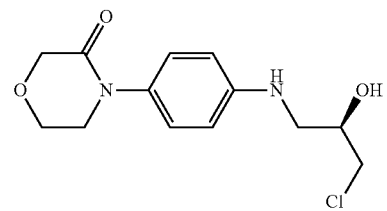

9a and the bromo- and iodo-analogues of the compounds of the general Formula 9 i.e. the compounds of the Formula

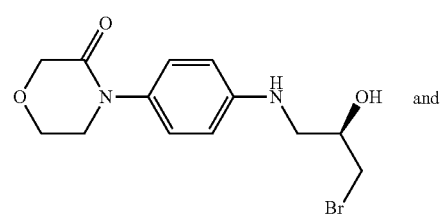

9b and

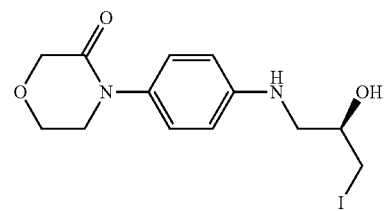

9c can be prepared from the compound of the Formula 9a in a manner known from prior art.

In the second step of the reaction route shown on reaction scheme 7b the preparation of the compounds of the general Formula 14 are prepared by reacting a compound of the general Formula 10 (wherein $L^2$ is as stated above) with a compound of the general Formula $Z^1Z^2NH$ (wherein $Z^1$ and $Z^2$ are as stated above). The reaction is carried out in the absence or presence of a solvent, in the presence of an organic or inorganic acid binding agent, preferably cesium carbonate at a temperature of 0-150° C. preferably 60-100° C.

The further reaction steps—the two last steps—shown on reaction scheme 7b are identical with the two last steps shown on reaction scheme 7a.

A preferred embodiment of the invention process for the preparation of rivaroxaban of the Formula 1 is shown on reaction scheme 8a.

On reaction schema 7a and 8a we have indicated the chirality of the intermediates according to the Cahn-Ingold-Prelog nomenclature.

The new synthesis route has also been performed by using the racemic forms of the compounds shown on reaction scheme 8a, starting from epichlorohydrine. The racemic compounds corresponding to the intermediates of the Formula

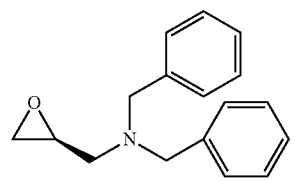

17

18, 13 and 3b are susceptible to salt formation and thus their corresponding enantiomers can be obtained by resolution.

Resolution is carried by conventional methods known from prior art with the aid of an enzyme, or kinetic resolution or diastereomeric salt formation and subsequent separation of the diastreomeic derivatives by chromatography or fractional crystallization or physical methods.

From the compounds shown on reaction scheme 8a
4-(4-amino-phenyl)-morpholine-3-one of the Formula 5
(2S)-chloromethyl-oxirane, well-known name epichlorohydrine, of the Formula 11
N-benzyl-1-phenylmethyneamine, well-known name dibenzyl amine, of the Formula 16
(2S)—N,N-dibenzyl-1-oxirane-2-yl-methaneamine of the Formula 17 and
5-chloro-thiophen-2-carboxylic acid of the Formula 15 and
rivaroxaban of the Formula 1
are known from prior art the compounds 1, 5, 11, 16 and 15 are commercially available.

The 4-(4-amino-phenyl)-morpholine-3-one of the Formula 5 is disclosed in EP 11261606, WO 2004/101556, WO 2005/026135, WO 2006/0632193 and the publication IPCOM0000195906D published in 2010 in IP.com Journal. The (S)-epichlorohydrine of the Formula 11 and racemic form thereof, the dibenzyl amine of the Formula 16 and 5-chloro-thiophen-2-carboxylic acid of the Formula 15 are commercially available. The (2S)—N,N-dibenzyl-oxirane-2-yl-methaneamine of the Formula 17 is described in CP 20032005282. The preparation of the racemic form of the compound of the Formula 17 is disclosed—among others—in U.S. Pat. No. 4,656,180.

From the intermediates shown on reaction schema 8a
4-(4-{[(2R)-3-(dibenzylamino)-2-hydroxy-propyl] amino}phenyl)morfolin-3 of the Formula 18
4-(4-{(5S)-5-[(dibenzylamino)methyl]-2-oxo-1,3-oxazo-lidine-3-il}phenyl)morfolin-3-one of the Formula 13 and
4-{4-[(5S)-5-(aminomethyl)-2-oxo-1,3-oxazolidine-3-il] phenyl}morpholine-3 acetic acid salt of the Formula 3b
and the racemic forms thereof have not become known from prior art.

The compounds of the Formulae 18 and 13 are susceptible to salt formation. Additionally the compounds of the Formulae 18 and 13 and the racemic equivalents thereof can exist in the form of solvates and can form co-crystals respectively. The invention also relates to the salts, solvates and hydrates of the compounds of the Formula 18 and 13 and racemates thereof and also to the co-crystals of said compounds.

The invention also relates to 4-(4-{[(2R)-3-dibenzylamino-2-hydroxy-propyl]-amino}-phenyl-morfoline-3-one of the Formula 18 and the racemic form thereof.

The invention also relates to the preparation of the compound of the Formula 18 starting from the compound of the Formula 17.

The invention also relates to the preparation of the racemic form of the compound of the Formula 18 starting from the racemic from of the compound of the Formula 17.

The invention also relates to compounds of the general Formula 20 and racemic forms thereof (wherein $Z^1$ and $Z^2$ stand for hydrogen or a protecting group with the proviso that at least $Z^1$ is other than hydrogen).

The invention also relates to a process for the preparation of the compounds of the general Formula 20 and racemic forms thereof starting from a compound of the general Formula 19 or a racemic form thereof.

The invention also relates to the compound 4-(4-{(5S)-5-[(dibenzylamino)-methyl]-2-oxo-1.3-oxazolidine-3-yl}-phenyl-morpholine-3-one of the Formula 13 and the racemic form thereof.

The invention also relates to a process for the preparation of the compound of the Formula 13 starting from the compound of the Formula 18.

The invention also relates to a process for the preparation of the racemic form of the compound of the Formula 13 starting from the racemic form of the compound of the Formula 18.

The invention also relates to the compounds of the general Formula 14 and racemic forms thereof (wherein $Z^1$ and $Z^2$ stand for hydrogen or a protecting group with the proviso that at least $Z^1$ is other than hydrogen).

The invention also relates to a process for the preparation of compounds of the general Formula 14 and racemic forms thereof, starting from compounds of the general Formula 20 and racemic forms thereof.

The invention also relates to a process for the preparation of the compound of the Formula 12 and the racemic form thereof starting from the compound of the Formula 14 or the racemic form thereof.

The invention also relates to the 4-{4-[(5S)-5-aminomethyl-2-oxo-1,3-oxazolidine-3-yl]-phenyl}-morpholine-3-one acetic acid salt of the Formula 3b and the racemic form thereof.

The invention also relates to a process for the preparation of the 4-{4-[(5S)-5-aminomethyl-2-oxo-1,3-oxazolidine-3-yl]-phenyl}-morpholine-3-one acetic acid salt of the Formula 3b and racemic form thereof starting from a compound of the Formula 13 or 14 or a racemic form thereof.

The invention also relates to a process for the preparation of rivaroxaban of the Formula 1 by reacting a compound of the general Formula 3 (wherein HnX stands for a mono- or polyvalent organic or inorganic acid; n represents 1, 2 or 3 and X is an acid residue ion) or the compound of the Formula 12 and the 5-chloro-thiophen-2-carboxylic acid of the Formula 15.

According to a preferred embodiment of the process (see reaction scheme 8a) the compound of the Formula 17 is prepared by reacting the compound of the Formula 11 with dibenzyl amine of the Formula 16 (in this case $Z^1$ and $Z^2$ stand for benzyl). The reaction is carried out in the absence of a solvent or in an organic solvent or water or a mixture thereof and preferably in the presence of an organic or inorganic acid binding agent.

According a preferred embodiment of the invention process the compound of the Formula 18 is prepared by reacting 4-amino-phenyl-morpholinone of the Formula 5 with (2S)—N,N-dibenzyl-1-oxirane-2-yl-methaneamine of the Formula 17. The reaction is preferably carried out in a protic solvent or solvent mixture or in a mixture of a protic solvent and water, at 0-150° C., preferably 60-90° C. for a period of 0.5-60 hours, preferably 20-40 hours.

The compound of the Formula 18 has a high melting point, crystallizes readily and is particularly suitable for use as an intermediate of industrial scale pharmaceutical manufacturing procedures. According to the process of the present invention said compound can be prepared without recrystallization in a chemical purity higher than 98% and with an excellent high enantiomer purity of 99%.

It is known from prior art that ring-opening of epoxide type compounds with nucleophiles results in the formation of a mixture of regioisomers depending on the fact whether the nucleophilic center (in the present case the amino group of the compound of the Formula 5) attacks which positively polarized carbon atom of the epoxy function of the compound of the Formula 17. Additionally, in reactions of this type, depending on the reaction conditions, there is the danger of partial or complete racemization on the chirality center. It has been surprisingly found that under the optimalized reaction conditions used in the process of the present invention the non-desired regioisomer is formed only to a very small extent, racemization practically does not take place and the compound of the Formula 18 obtained can be characterized by a chemical purity of 98.4% and a 99% e.e. value.

According to a preferred concrete embodiment of the present invention the racemic form of the compound of the Formula 18 is prepared by reacting 4-amino-phenyl-morpholinone of the Formula 5 with the racemic form of N,N-dibenzyl-1-oxirane-2-yl-methaneamine of the Formula 17. The reaction is carried out preferably in a protic solvent or solvent mixture or a mixture of a protic solvent and water, at 0-150° C. advantageously 40-80° C. for a period of time of 0.5-60 hours, preferably 40-50 hours.

According to the process of the present invention the racemic form of the compound of the Formula 18 can be prepared with very good yield. The compound has a high melting point, can be readily crystallized and is excellently suitable as intermediate in manufacturing procedures of pharmaceutical industry. Said product, when prepared according to the process of the present invention, can be used in the further steps of the synthesis without recrystallization.

Under the optimalized reaction conditions of the present invention the non-desired regioisomer is only formed in a very small amount and the intermediate prepared (racemic form of the compound of the Formula 18) can be used in the further steps of the synthesis without recrystallization.

According to a preferred concrete embodiment of the process according to the present invention the compound of the Formula 13 is prepared by reacting 4-(4-{[(2R)-3-dibenzylamino-2-hydroxy-propyl]-amino}-phenyl)-morfoline-3-one of the Formula 18 and an agent capable of introducing the carbonyl group, preferably N,N'-carbonyl-diimidazole, phosgene, diphosgene or triphosgene, particularly N,N'-carbonyl-diimidazole in a suitable solvent, preferably toluene.

The compound of the Formula 13 has a high melting point, can be easily crystallized and is highly suitable as an intermediate in the manufacturing procedure of pharmaceutical industry. According to the process of the present invention the compound of the Formula 13 can be prepared with an excellent yield, in a chemical purity of 99.9% and practically in an enantiomeric purity of 99.9%.

It is known from prior art that in reactions of this type instead of the desired intramolecular cyclization by-products can be formed in an intermolecular reaction because the C1 reactant used couples two molecules with each other through their NH and OH functions. Additionally—since in the starting material of the Formula 18 the hydroxyl group is attached to the chirality center—loss of water can result in the formation of by-products containing a double bond and also partial or complete racemization can take place. It has been found in a surprising manner that under the optimalized reaction conditions used in the process of the present invention the formation of by-products is very low and the compound of the Formula 13 obtained can be characterized by a chemical purity of 99.9% and a 99.9% e.e. value.

A preferred concrete embodiment of the invention process for the preparation of rivaroxaban of the Formula 1 is shown on reaction scheme 8b.

On reaction schema 7b and 8b the chirality of the intermediates according to the Cahn-Ingold-Prelog has been indicated.

As seen from reaction scheme 8b the starting material of the process is (2R(-chloromethyl-oxirane (well-known name (R(-epichlorohydrine (of the Formula 11 and from said compound in six steps rivaroxaban of the Formula 1 having the (S(configuration is obtained. In the reaction step 10b (10c)→13 the configuration is only apparently changed, however actually this is not an inversion step but the conversion of the (R) chirality into (S) chirality is only a change of nomenclature derived from the new group hierarchy following the introduction of a new structural unit.

From the compounds shown on reaction scheme 8b
the 4-(4-amino-phenyl)-morpholine-3-one of the Formula 5
the (2S)-chloromethyl-oxirane (well-known name (S)-epichlorohydrine) of the Formula 11
N-benzyl-1-phenylmethaneamine (well-known name dibenzyl amine) of the Formula 16
5-chloro-thiophen-2-carboxylic acid of the Formula 15 and
rivaroxaban of the Formula 1
are known from the art or commercially available.

From the intermediates and direct analogues thereof shown on the reaction scheme 8b
4-{4-[((2R)-3-chloro-2-hydroxypropyl)-amino]-phenyl}-morpholine-3-one of the Formula 9a
4-{4-[((2R)-3-bromo-2-hydroxypropyl)-amino]-phenyl}-morpholine-3-one of the Formula 9b (this is a compound of the Formula 9 wherein $L^2$ is bromine)
4-{4-[((2R)-3-iodo-2-hydroxypropyl)-amino]-phenyl}-morpholine-3-one (compound of the general Formula 9c wherein $L^2$ is iodine)
4-{4-[(5R)-5-chloromethyl-2-oxo-1,3-oxazolidine-3-yl] phenyl}-morpholine-3-one of the Formula 10a
4-{4-[(5R)-5-bromomethyl-2-oxo-1,3-oxazolidine-3-yl]-phenyl}-morpholine-3-one of the Formula 10b and
4-{4-[(5R)-4-iodomethyl-2-oxo-1,3-oxazolidine-3-yl]-phenyl}-morpholine-3-one of the Formula 10c
fall under a general Formula in WO 2010/124385, however there is no reference to the preparation thereof and the physical constants suitable for identification of these compounds are not disclosed either.

From the intermediates shown on the reaction scheme 8b
4-(4-{(5S)-5-(dibenzylamino-methyl]-2-oxo-1,3-oxazolidine-3-yl}-phenyl-morpholine-3-one of the Formula 13 and
4-{4-[(5S)-5-aminomethyl-2-oxo-1,3-oxazolidine-3-yl]-phenyl}-morpholine-3-one acetic acid salt of the Formula 3 are not known from prior art.

As reference we have carried out the reaction sequence by starting from the commercially available (S)-epichlorohydrine of the Formula 11S and obtained the enantiomer of rivaroxaban of the Formula 1R, namely the (5-chloro-N-({(5R)-2-oxo-3-[4-(3-oxo-morpholine-4-yl)-phenyl]-1,3-oxazolidine-5-yl}-methyl(methyl)-thiophen-2-carboxamide (see reaction scheme 9).

From the intermediates shown on reaction scheme 9
4-{4-[((2S)-3-chloro-2-hydroxypropyl)-amino]-phenyl}-morpholine-3-one of the Formula 9aS
4-{4-[(5S)-5-chlomethyl-2-oxo-1,3-oxazolidine-3-yl]-phenyl}-morpholine-3-one of the Formula 10aS
4-{4-[(5S)-5-iodomethyl-2-oxo-1,3-oxazolidine-3-yl]-phenyl}-morpholine-3-one of the Formula 10cS 4-(4-{(5R-5-[(dibenzylamino-methyl]-2-oxo-1,3-oxazolidine-3-yl}-phenyl)-morpholine-3-one of the Formula 13R and 4-{4-[(5R-5-aminomethyl-2-oxo-1,3-oxazolidine-3-yl]-phenyl}-morpholine-3-one acetic acid salt of the Formula 3bR were not described in prior art.

We have also carried out the synthesis sequence starting from the commercially available (±)-epichlorohydrine of the Formula rac11 and obtained the racemic equivalent of rivaroxaban of the Formula rac1 (see reaction sequence 10).

From the intermediates shown on reaction scheme 10

4-{4-[(3-chloro-2-hydroxypropyl)-amino]-phenyl}-morpholine-3-one of the Formula rac9a 4-{4-[5-chloromethyl-2-oxo-1,3-oxazolidine-3-yl]-phenyl}-morpholine-3-one of the Formula rac10a 4-{4-[5-iodomethyl-2-oxo-1,3-oxazolidine-3-yl]-phenyl}-morpholine-3-one of the Formula rac10c 4-[4-[5-(dibenzylamino-methyl)-2-oxo-1,3-oxazolidine-3-yl]-phenyl}-morpholine-3-one of the Formula rac13 and 4-(-{4-[5-aminomethyl-2-oxo-1,3-oxazolidine-3-yl]-phenyl}-morpholine-3-one acetic acid salt of the Formula rac3b are not described in prior art.

The compounds of the Formulae rac9a, rac13 and rac3b contain a basic nitrogen and therefore by resolution potentially suitable enantiomers can be obtained which can be used for the preparation of rivaroxaban of the Formula 1 as shown on reaction scheme 8b by using methods known from prior art.

Resolution can be carried out by conventional methods e.g. by using an enzyme, kinetic resolution, diastereomeric salt formation and subsequent separation of the diastereomeric derivatives by means of chromatography or fractional crystallization or by physical methods.

The compounds of the Formulae 9a and 13 and enantiomers and racemic forms thereof can form salts. Additionally the compounds of the Formulae 9a, 10a, 10b, 10c and 13 and enantiomers and racemic forms thereof can also exist in the form of hydrates and other solvates and can also form co-crystals. The invention also relates to compounds of the Formulae 9a, 10a, 10b, 10c and 13 and enantiomers, and racemates thereof and salts, hydrates, solvates and co-crystals thereof.

The invention also relates to 4-{4-[((2R)-3-chloro-2-hydroxypropyl)-amino]-phenyl}-morpholine-3-one of the Formula 9a (compound of the Formula 9 wherein $L^2$ is chlorine) and the racemic form thereof.

The invention also relates to 4-{4-[((2R)-3-bromo-2-hydroxypropyl)-amino]-phenyl}-morpholine-3-one of the Formula 9b (this is a compound f the Formula 9 wherein $L^2$ is bromine) and the racemic form thereof.

The invention also relates to 4-{4-[((2R)-3-iodo-2-hydroxypropyl)-amino]-phenyl}-morpholine-3-one of the Formula 9c (compound of the general Formula 9 wherein $L^2$ is iodine) and the racemic form thereof.

According to the present invention there is also provided a process for the preparation of the compound of the Formula 9a and the racemic form thereof starting from the compound of the Formula 11 or the racemate thereof.

According to the present invention there is also provided the compound 4-{4-[(5R)-5-chloromethyl-2-oxo-1,3-oxazolidine-3-yl]phenyl}morpholine-3-one of the Formula 10a and the racemic form thereof.

According to the present invention there is also provided the compound 4-{4-[(5R)-5-bromomethyl-2-oxo-1,3-oxazolidine-3-yl]phenyl}morpholine-3-one of the Formula 10b and the racemic form thereof.

According to the present invention there is also provided the compound 4-{4-[(5R)-5-iodomethyl-2-oxo-1,3-oxazolidine-3-yl]phenyl}morpholine-3-one of the Formula 10c and the racemic form thereof.

According to the present invention there is also provided a process for the preparation of the compound of the Formula 10a and the racemic form thereof starting from the compound of the Formula 9a or the racemic form thereof.

According to the present invention there is also provided a process for the preparation of the compound of the Formula 10b and the racemic form thereof starting from the compound of the Formula 9b or the racemic form thereof.

According to the present invention there is also provided a process for the preparation of the compound of the Formula 10c and the racemic form thereof starting from the compound of the Formula 9c or the racemic form thereof.

According to the present invention there is also provided a process for the preparation of the compound of the Formula 10b and the racemic form thereof starting from the compound of the Formula 10a or a racemic form thereof.

According to the present invention there is also provided a process for the preparation of the compound of the Formula 10c and the racemic form thereof starting from the compound of the Formula 10a or a racemic form thereof.

According to the present invention there is also provided a process for the preparation of the compound of the Formula 13 and the racemic form thereof starting from a compound of the Formula 10a, 10b or 10c or a racemic form thereof.

According to the present invention there is also provided a process for the preparation of the compound of the Formula 14 and the racemic form thereof starting from a compound of the Formula 10a, 10b or 10c or a racemic form thereof.

According to a preferred concrete embodiment of the invention process (see reaction scheme 8b) the compound of the Formula 9a is prepared by reacting 4-amino-phenyl-morpholine of the Formula 5 with epichlorohydrine of the Formula 11 in an organic solvent or a mixture of a water-miscible organic solvent and water at a temperature of 0-150° C., preferably at the reflux temperature of the solvent or solvent mixture for 0.5-60 hours.

The compounds of the general Formula 9 have a high melting point, can be readily crystallized and are particularly suitable for use as intermediate of manufacturing procedures of pharmaceutical industry. According to the process of the present invention the compound of the Formula 9a can be prepared without recrystallization in a chemical purity higher than 95% and an outstanding enantiomeric purity of above 99%.

It is known from prior art that the ring-opening of epoxide type compounds with nucleophiles leads to the formation of a mixture of regioisomers depending on the fact whether the nucleophile center (in the present case the amino group of the compound of the Formula 5) attacks which positively polarized carbon atom of the epoxy function of the corresponding compound of the Formula 11. Additionally in reactions of this type—in case of optically active starting materials—depending on the reaction conditions there is a risk of partial or complete racemization on the chirality center. It has been surprisingly found that under the optimalized reaction conditions according to the present invention the non-desired regioisomer is only formed in a very small amount. When optically active starting materials are used racemization does not practically take place.

According to an other preferred concrete embodiment of the present invention the compound of the Formula 10a is prepared by reacting the compound of the Formula 9a with an agent capable of introducing the carbonyl group, preferably N,N'-carbonyl-diimidazole, phosgene, diphosgene or triphosgene, particularly N,N'-carbonyl-diimidazole in a suitable solvent or solvent mixture, preferably in toluene, 1-methyl-2-pyrrolidone or a mixture thereof at 0-150° C., preferably at the reflux temperature of the solvent or solvent mixture.

The compounds of the general Formula 10 have a high melting point, can be readily crystallized and are particularly suitable for use as intermediate of manufacturing procedures of pharmaceutical industry. According to the process of the present invention these compounds can be prepared in a chemical purity of 95% and an enantiomeric purity higher than 99% without recrystallization. The compound of the Formula 10c can be prepared from the compound of the Formula 10a with a high yield of 95.2%.

It is known from prior art that in course of reactions of this type in place of the desired intramolecular ring-closure an intermolecular reaction takes place and by-products can be formed because the C1 agent used couples two molecules through their NH and OH functions. Additionally—since in the starting materials of the general Formula 9 the hydroxy group is attached to the chirality center-loss and further uptake of water can lead to the formation of by-products containing a double bond and partial or complete racemization can also take place. We have found in a surprising manner that under the optimalized reaction conditions of the present invention by-products are formed only in a very small extent and racemization does not even occur.

According to a preferred concrete embodiment of the present invention the compound of the Formula 10c is prepared from the compound of the Formula 10a by reacting said compound of the Formula 10a with an alkali iodide, preferably sodium iodide, in a suitable solvent or solvent mixture, preferably in a mixture of an organic solvent and water, at 0-150° C., preferably at 80-130° C.

According to an other preferred concrete embodiment of the present invention the compound of the Formula 10b is prepared from the compound of the Formula 10a by reacting said compound of the Formula 10a with an alkali bromide preferably sodium bromide, in a suitable organic solvent or solvent mixture, at 0-150° C. preferably at 80-130° C.

According to a preferred concrete embodiment of the present invention the compound of the Formula 13 is prepared by reacting a compound of the Formula 10a, 10b or 10c of appropriate chirality, preferably the compound of the Formula 10c of appropriate chirality with dibenzyl amine of the Formula 16, in this case $Z^1$ and $Z^2$ stand for benzyl) in the presence or absence of a solvent, in the presence of cesium carbonate, at 0-150° C., preferably at 60-100° C., whereupon the reaction mixture is worked up and the product obtained is subjected to further purification if desired.

The compound of the Formula 13 has a high melting point, can be readily crystallized and is particularly suitable for use as intermediate of manufacturing procedures of pharmaceutical industry. According to an other process of the present invention (reaction scheme 8b) this compound can be prepared after recrystallization in an outstanding chemical purity higher than 99.5% and an enantiomeric purity of 99.9%.

It is known from prior art that in nucleophilic substitution ($S_N$) reaction of this type—in case of optically active starting materials—depending on the reaction conditions—there is a danger of partial or complete racemization on the chirality center or of an inversion, respectively. As a characteristic side reaction hydrogen halide is split off due to the basicity of the nucleophilic agent (in the present case dibenzyl amine). We have found in a surprising manner that under the used optimalized reaction conditions according to the present invention no detectable elimination side reaction takes place and in case of optically active starting material neither inversion nor racemization occurs.

The last two steps of the procedures shown on reaction schema 8a and 8b are identical and for this reason the last two steps of the two preferred concrete embodiments of the present invention are discussed together.

According to a preferred concrete embodiment of the process of the present invention the compound of the Formula 3b is prepared by subjecting 4-(4-{(5S)-[dibenzylamino-methyl]-2-oxo-1,3-oxazolidine-3-yl}-phenyl)-morpholine-3-one of the Formula 13 to catalytic hydrogenation or chemical reduction in a C1-4 aliphatic alcohol, glacial acetic acid, water or a mixture of said solvents formed with each other or with other organic solvents, working up the reaction mixture and separating the product by adding acetic acid in the form of the salt of the Formula 3b.

According to an other preferred concrete embodiment the compound of the Formula 3b is prepared by converting 4-(4-{(5S)-5-aminomethyl-2-oxo-1,3-oxazolidine-3-yl]-phenyl}-morpholine-3-one of the Formula 12 obtained by any synthesis route known from prior art or described in the present patent application into the salt of the Formula 3b by adding acetic acid.

The compound of the Formula 3b has a high melting point, can be easily crystallized and is particularly suitable as intermediate of pharmaceutical manufacturing procedures. When prepared according to the process of the present invention said compound is obtained with a very high yield (98%), in an outstanding chemical purity (99.5%) and a high enantiomeric purity (99.9%) without recrystallization.

According to a preferred concrete embodiment of the process of the present invention rivaroxaban of the Formula 1 is prepared by reacting the acetic acid salt of 4-(4-((5S(-5-aminomethyl-2-oxo-1,3-oxazolidine-3-yl)-phenyl)-morpholine-3-one of the Formula 3b with 5-chloro-thiophen-2-carboxylic acid of the Formula 15 in the presence of a coupling agent and an organic or inorganic base, in an organic solvent. As coupling agent chloro ethyl formiate, N,N-diisopropyl-carbodimide (DIC), N,N'-dicyclohexyl-carbodiimide (DCC) tripropyl-phosphonic anhydride (T3P) or N,N'-carbonyl-diimidazole, preferably chloro ethyl formiate or CDI can be used. As solvent acetonitrile, dichloro methane, acetone, toluene, tetrahydrofurane or a mixture thereof or a mixture of said organic solvent formed with water can be applied. As organic or inorganiv base triethyl amine, diisopropyl ethyl amine, sodium carbonate or sodium hydrogen carbonate can be used. The reaction is carried out at a temperature between 0-110° C. and 110° C., preferably at 40-70° C. The use of the acid binding agent can be optionally omitted.

The advantage of the process of the present invention is that the intermediates have high melting point, can be readily crystallized and are excellently suitable as intermediates of pharmaceutical manufacturing procedures. Said compounds can be prepared according to the process of the present invention in outstandingly high chemical and enantiomeric purity without recrystallization.

Thus e.g. the compounds of the Formulae 13 and 3b can be prepared according to the process shown on reaction scheme 8b without recrystallization in a chemical purity above 95%—for the compound of the Formula 13 preferably 99.4% and in an enantiomeric purity higher than 99%—for the compounds of the Formulae 13 and 3b preferably 99.9%.

A further advantage of the invention process resides in the high yields of the reaction steps.

A further advantage of the invention process is that from the 4-{4-[(5S)-5-(dibenzylamino-methyl)-2-oxo-1,3-oxazolidine3-yl]-phenyl}-morpholine-3-one intermediate of the Formula 13 the protecting group can be removed under much milder conditions than the phthalyl protecting group used according to WO 2005/068456 (see reaction scheme 4 (and therefore the last intermediate of the Formula 3b of the synthesis route can be prepared in a higher purity than described in said prior art.

A further advantage of the process of the present invention is that the reactant of the Formula 15 used in the last acylation step of the preparation of rivaroxaban of the Formula 1 of is more advantageous in several properties than the acid chloride of the Formula 4. These advantages are as follows:

the compound of the Formula 15 is solid and crystalline while the compound of the Formula 4 is a viscous substance difficult to handle, the compound of the Formula 15 is stable while the compound of the Formula 4 easily hydrolyses, the effective amount content thereof decreases gradually on storage, even when stored at 0-5° C., in the preparation of the compound of the Formula 15 the use of the corrosive, thionyl chloride which has an unpleasant odor and can be only difficultly removed can be eliminated and the treatment with poisonous gases detrimental to the environment formed in the thionyl chloride reaction can be avoided, the synthesis route is shorter by one step, the compound of the Formula 15 is a significantly cheaper reactant than the compound of the Formula 4.

Further advantages of the process of the present invention over the process described in WO 2011/012321, which also uses 5-chloro-thiophen-2-carboxylic acid of the Formula 15 are as follows: by selecting a more suitable solvent and using more advantageous reactive conditions and applying the acetic acid salt of the Formula 3b in the place of the hydrochloric acid salt contrary to the crude yield of 72% disclosed in WO 2011/012321 according to the invention process a yield of 87% can be achieved. After recrystallization the total yield according to WO 2011/012321 amounts to 61% while that according to the present invention to 70%. In WO 2011/012321 no purity data are set forth while the HPLC purity of the product obtained according to the invention process is 99.32%.

A further advantage of the invention process is that from the acetic acid medium used by the catalytic debenzylation reaction (13→3b) the acetic acid salt of the Formula 3b can be directly isolated with an extremely high yield (98%), in a chemical purity of 99.91% and an enantiomeric purity of 99.9%. Thus the process of the present invention is directly suitable for the preparation of the end-product of the Formula 1 which is pure and meets the purity requirements of pharmaceutical industry.

A further advantage of the process shown on reaction scheme 8a is that under the optimized reaction conditions used in the preparation of the compound of the Formula 18 the non-desired regioisomer is formed but to a very small extent and racemization did not practically take place. Thus the compound of the Formula 18 is obtained in a chemical purity of 98.4% and can be characterized by a 99% e.e. value.

An additional advantage of the process shown on reaction scheme 8a is that under the optimized reaction conditions used in the preparation of the compound of the Formula 13 the by-products are formed only to a very small extent and racemization does not take place at all. Thus the compound of the Formula 18 is obtained in a chemical purity of 99.9% and can be characterized by a 99% e.e. value.

A further advantage of the process shown on reaction schema 7b and 8b is that under optimized reaction conditions used in the reaction of the compounds of the Formula 11 and 5 the formation of the non-desired regioisomer is very small and, and if optically active starting material is used, racemization does not practically take place.

A further advantage of the process shown on reaction schema 7b and 8b is that under the optimized reaction conditions used in the preparation of the compound of the Formula 10 by-products are formed only to a very small extent and racemization does not take place at all.

A further advantage of the process shown on reaction schema 7b and 8b is that under the optimized reaction conditions used in the preparation of the compound of the Formula 13 no detectable elimination side-reaction took place and, if optically active starting materials were used, racemization did not take place at all.

A further advantage of the process according to the present invention as shown on reaction schema 7a, 7b, 8a and 8b is that it provides a synthesis route for the preparation of the rivaroxaban of the Formula 1 which is more efficient and more suitable for industrial scale manufacture than methods the for the preparation of rivaroxaban of the Formula 1 known from prior art.

Further details of the present invention are to be found in the following Example without limiting the scope of protection to said Examples.

Example 1

Preparation of
(2S)—N,N-dibenzyl-1-oxirane-2-yl-methanamine of the Formula 17

To a solution of 49.25 g (48 ml, 0.25 mole) of dibenzyl amine (compound of the Formula 16) in 40 ml of 2-propanol at 0° C. 25.44 g (21.56 ml, 0.275 mol) of (S)-epichlorohydrine (compound of the Formula 11) are added dropwise under stirring. The addition having been completed the reaction mixture is allowed to warm to room temperature and is stirred for 24 hours. To the reaction mixture 90 ml of 2-propanol are added and the mixture is cooled to 0° C. To the reaction mixture in portions 112.0 g (2.0 moles) of potassium hydroxide are added, the temperature is kept at 0° C., after termination of the addition the reaction mixture is stirred for a further period of 30 minutes, whereupon 250 ml of distilled water and 150 ml of hexane are added. The phases are separated, the aqueous layer is extracted three times with 100 ml of hexane each, the united organic phases are washed twice with 150 ml of water each, dried over magnesium sulfate and the solvent is removed in vacuo. Thus in the form of an oil 62 g (98.5%) of the desired product are obtained, HPLC purity 95.8%, e.e. 99.15%.

IR (film): 3062, 2797, 1494, 1453, 746, 699 cm$^{-1}$.

$^1$H NMR (CDCl$_3$, 500 MHz): 7.38 (m, 4H), 7.30 (m, 4H), 7.22 (m, 2H), 3.79 (d, J=13.7 Hz, 1H), 3.56 (d, J=13.6 Hz, 1H), 3.06 (m, 1H), 2.75 (dd, J$_1$=3.7 Hz, J$_2$=13.7 Hz, 1H), 2.65 (dd, J$_1$=4.2 Hz, J$_2$=4.9 Hz, 1H), 2.43 (dd, J$_1$=6.2 Hz, J$_2$=13.7 Hz, 1H), 2.39 (dd, J$_1$=2.7 Hz, J$_2$=4.9 Hz, 1H) ppm.

$^{13}$C NMR (CDCl$_3$, 125 MHz): 139.3, 128.8, 128.2, 126.9, 58.9, 55.8, 51.0, 45.0 ppm.

Elementary analysis for the Formula C$_{17}$H$_{19}$NO (M: 253.35): C, 80.60; H, 7.56; N, 5.53%. Found: C, 78.90; H, 8.04; N, 5.45%.

Rotation: [α]$^{20}_D$=+5.12° (588 nm/20° C.; c=0.05 g/10 cm$^3$ DMSO)

Example 2

Preparation of 4-(4-{[(2R)-3-dibenzylamino-2-hydroxy-propyl]-amino}-phenyl)-morfoline-3-one of the Formula 18

19.2 g of 4-amino-phenyl-morpholinone (compound of the Formula 5) are suspended in a mixture of 150 ml of 2-propanol and 5 ml of distilled water at 25° C. whereupon 25.3 g (0.1 mole) of (2S)—N,N-dibenzyl-1-oxirane-2-yl-methaneamine (compound of the Formula 17) are added. The reaction mixture is warmed to 80-82° C. and stirred at this temperature for 44 hours. In the 18$^{th}$ hour 12.6 g (0.05 mole) of (2S)—N,N-dibenzyl-1-oxirane-2-yl-methaneamine are added to the reaction mixture. After 44 hours the reaction mixture is allowed to cool to room temperature, stirred in an ice-cold bath for an hour and the precipitated solid is filtered off. The product is washed on the filter with 50 ml of 2-propanol and dried under an infrared lamp to constant weight. Thus 23.4 g (53%) of a white solid product are obtained, HPLC purity 98.4%: e.e. 99.40%. Mp.: 179-180° C.

Mp.: 179-180° C.

IR (KBr): 3372, 1623, 1528, 1103, 749, 699.

HNMR (DMSO, a400): 7.37 (m, 4H), 7.32 (m, 4H), 7.24 (m, 2H), 7.01 (~d, J=8.7 Hz, 2H), 6.53 (~d, J=8.5 Hz, 2H), 5.37 (bt, J=5.8 Hz, 1H), 4.68 (d, J=4.8 Hz, 1H), 4.13 (s, 2H), 3.93 (m, 2H), 3.85 (m, 1H), 3.67 (d, J=13.7 Hz, 2H), 3.60 (m, 2H), 3.53 (d, J=13.7 Hz, 2H), 3.15 (m, 1H), 2.75 (m, 1H), 2.50 (m, 2H).

CNMR: 165.89, 147.66, 139.42, 130.34, 128.82, 128.31, 126.98, 126.54, 111.98, 67.91, 67.10, 63.72, 58.57, 57.87, 49.76, 48.25, 39.70.

Elementary analysis for the Formula C$_{27}$H$_{31}$N$_3$O$_3$ (M: 445.57): C, 72.78; H, 7.01; N, 9.43%. Found: C, 72.39; H, 6.97; N, 9.49%.

Rotation: [α]$^{20}_D$=−13.83° (588 nm/20° C.; c=0.1 g/10 cm$^3$ DMSO)

Example 3

Preparation of 4-(4-{(5S)-5-(dibenzylamino-methyl]-2-oxo-1,3-oxazolidine-3-yl}-phenyl)-morpholine-3-one of the Formula 13

I 23 g (51 millimoles) of 4-(4-{[(2R)3-dibenzylamino-2-hydroxypropyl](-amino}-phenylmorpholine-3-one (compound of the Formula 18) and 10.19 g (63 millimoles) of N,N'-carbonyl-diimidazole are suspended in 70 ml of toluene at 25° C. The mixture is warmed to 80-83° C. and stirred at this temperature for 20 minutes. The reaction mixture is cooled to 60° C. and 230 ml of ethanol are added dropwise. The reaction mixture is allowed to cool to room temperature, stirred in a an ice-cold bath or an hour, whereupon the precipitated solid substance is filtered off and dried under an infrared lamp to constant weight. Thus 22.3 g (93%) of a white solid substance are obtained, HPLC purity 99.92%, e.e. 100%, mp.: 154-155° C.

IR (KBr): 1732, 1653, 1521, 1415 cm$^{-1}$.

$^1$H NMR (DMSO-d$_6$, 400 MHz): 7.48 (d, J=9.1 Hz, 2H), 7.39 (d, J=9.1 Hz, 2H), 7.36 (m, 4H), 7.32 (m, 4H), 7.24 (m, 2H), 4.83 (m, 1H), 4.20 (s, 2H), 4.03 (m, 1H), 3.97 (m, 2H), 3.72 (m, 2H), 3.68 (d, J=4.39 Hz, 2H), 3.65 (d, J=13.8 Hz, 2H), 3.57 (m, 1H), 2.80 (m, 1H), 2.74 (m, 1H) ppm.

$^{13}$C NMR (DMSO-d$_6$, 100 MHz): 166.1, 154.3, 139.0, 137.2, 136.6, 128.9, 128.4, 127.2, 126.0, 118.5, 71.3, 67.9, 63.6, 58.3, 55.9, 49.2, 48.2 ppm.

Elementary analysis for the Formula C$_{28}$H$_{29}$N$_3$O$_4$ (M: 471.56): C, 71.32; H, 6.20; N, 8.91%. Found: C, 70.95; H, 6.30; N, 9.09%.

Rotation: [α]$^{20}_D$=−19.7° (588 nm/20° C.; c=0.1 g/10 cm$^3$ DMSO)

II

One proceeds according to the process described in I except that after having suspended 23 g (51 millimoles) of 4-(4-{[(2R)-3-dibenzylamino-2-hydroxypropyl]-amino}-phenyl)-morpholine-3-one (compound of the Formula 18) and 10.19 g (63 millimoles) of N,N'-carbonyl-diimidazole in 70 cm$^3$ of toluene at 25° C., the mixture is immediately heated to the boiling point.

Example 4

Preparation of the salt of 4-{4-[(5S)-5-aminomethyl-2-oxo-1,3-oxazolidine-3-yl]-phenyl}-morpholine-3-one formed with acetic acid (compound of the Formula 3b)

18.28 g (0.039 mole) of 4-(4-{(5S)-5-(dibenzylamino-methyl]-2-oxo-1,3-oxazolidine-3-yl}-phenyl)-morpholine-3-one of the Formula 13 are dissolved in 200 ml of glacial acetic acid at room temperature. To the solution 1.8 g of a 10% palladium-charcoal catalyst are added and hydrogenation is carried out in an autoclave at a hydrogen pressure of 10 bar for 24 hours. Hydrogenation having been completed the catalyst is filtered off, the filtrate is evaporated to dryness and from the residue four times 100 ml of ethanol each are distilled off at a pressure of 75 mbar. To the residue thus obtained 50 ml of ethanol are added, the mixture is stirred in a cooling bath for 30 minutes. The precipitated solid substance is filtered, washed with 30 ml of ethanol on the filter and dried under an infrared lamp to constant weight Thus 13.28 g (98%) of a white product are obtained.

Mp.: 142-143° C.

IR (KBr): 2557, 1747, 1725, 1650, 1524, 1413 cm$^{-1}$.

$^1$H NMR (DMSO-d$_6$, 500 MHz): 7.58 (d, J=8.8 Hz, 2H), 7.40 (d, J=8.6 Hz, 2H), 5.27 (br s, 3H), 4.65 (m, 1H), 4.19 (s, 2H), 4.08 (m, 1H), 3.96 (m, 2H), 3.87 (m, 1H), 3.71 (m, 2H), 2.88 (m, 2H), 1.88 (s, 3H) ppm.

$^{13}$C NMR (DMSO-d$_6$, 125 MHz): 172.5, 166.1, 154.5, 137.1, 136.9, 126.1, 118.4, 73.7, 67.9, 63.7, 49.2, 47.3, 44.1, 21.6 ppm.

Elementary analysis for the Formula C$_{16}$H$_{21}$N$_3$O$_6$ (M: 351.36): C, 54.70; H, 6.02; N, 11.96%. Found: C, 54.42; H, 6.05; N, 12.00%.

Rotation: $[\alpha]^{20}_D = -29.65°$ (588 nm/20° C.; c=0.1 g/10 cm$^3$ DMSO)

Example 5

Preparation of Rivaroxaban of the Formula 1

A solution of 0.13 g (11.25 millimoles) of sodium carbonate in 1.6 ml of water is cooled to 10° C. under stirring whereupon 0.35 g (1.0 millimoles) of the acetic acid salt of 4-{4-[(5S)-5-aminomethyl-2-oxo-1,3-oxazolidine-3-yl]-phenyl}-morpholine-3-one (compound of the Formula 3b) and 0.7 ml of acetone are added. The reaction mixture is kept at a temperature of 8-12° C. and a toluene solution of 0.62 g of a 32.5 vol. % toluene solution of 5-chloro-thiophen-2-carboxylic acid-chloride (4) and thereafter 0.7 ml of toluene are added. The reaction mixture is warmed to 50° C., 0.7 ml of acetone are added and the mixture is stirred for as further period of 30 minutes at 50-55° C. The reaction mixture is cooled to 26° C., the precipitated product is filtered, washed with 5 ml of water and 2.5 ml of acetone and dried under an infrared lamp to constant weight. Thus 0.38 g (87%) of the crude product is obtained, HPLC purity 98.8%, mp.: 227° C. On recrystallization the product from a 5.7-fold amount of glacial acetic acid 0.32 g of the white end-product is obtained, HPLC purity 99.5%, mp. 229° C.

Example 6

Preparation of Rivaroxaban of the Formula 1

I 11.9 g (12 millimoles) of 5-chloro-thiophen-2-carboxylic acid (15) and 1.9 g (12 millimoles) of N,N'-carbonyl-diimidazole are dissolved in 50 ml of dried acetonitrile. The reaction mixture is stirred at 50-55° C. for an hour, whereupon at this temperature 0.78 g (7.5 millimoles) of sodium carbonate, 3.4 g (9.67 millimoles) of 4-{4-[(5S)-5-aminomethyl-2-oxo-1,3-oxazolidine-3-yl]-phenyl}-morpholine-3-one acetic acid salt (3b) and 1 ml of distilled water are added. The reaction mixture is stirred at 50° C. for an hour and allowed to cool to room temperature. The solid substance is filtered and dried under an infrared lamp to constant weight. Thus 3.65 g (86.5%) of a crude product are obtained. The crude product is recrystallized from 22 ml of glacial acetic acid to yield 3.24 g (89%) of the white end-product, HPLC purity 99.3%, mp.: 230-231° C.

II

One proceeds as described in Par. I except that as base 0.8 g (8 millimoles) of triethyl amine are used. The quality of the crude product prepared (33.42 g, 81%) is identical with that of the crude product obtained according to the process of process I.

III

One proceeds as described in Par. I except that no acid binding agent is used (in process I sodium carbonate is applied). The quality of the crude product obtained (3.25 g, 77%) is identical with that of the crude product prepared according to process I.

Example 7

Preparation of racemic 4-(4-{[(3-dibenzylamino-2-hydroxy-propyl]-amino}-phenyl)-morfoline-3-one of the Formula 18 (racemic form of the compound of the Formula 18)

10.0 g (50 millimoles) of 4-amino-phenyl-morpholinone (compound of the Formula 5) and 2.0 g of lithium bromide are suspended in a mixture of 65 ml of 2-propanol and 26 ml of distilled water at 25° C. whereupon 13.0 g (50 millimoles) of N,N-dibenzyl-1-oxirane-2-yl-methaneamine (racemic form of the compound of the Formula 17) are added. The reaction mixture is warmed to 58-62° C. and stirred at this temperature for 48 hours. In the 18$^{th}$ hour a further 4.0 g (15.7 millimoles) and in the 42$^{nd}$ hour a further 2.0 g (7.9 millimoles) of N,N-dibenzyl-1-oxirane-2-yl-methaneamine are added. After 48 hours the reaction mixture is allowed to cool to room temperature, the precipitated product is filtered, washed with 15 ml of a 2:5 mixture of distilled water and 2-propanol and dried under an infrared lamp to constant weight. Thus 18.8 g (84%) of a white solid product are obtained. Mp.: 154-155° C.

Example 8

Racemic 4-(4-{(5S)-5-(dibenzylamino-methyl]-2-oxo-1,3-oxazolidine-3-yl}-phenyl)-morpholine-3-one of the Formula 13 (racemic form of the compound of the Formula 13)

I 0.90 g (2 millimoles) of 4-(4-{[2R/-3-dibenzylamino-2-hydroxypropyl]-amino}-phenyl)-morfoline-3-one of the racemic form of the compound of the Formula 18 and 0.338 g (3 millimoles) of N,N'-carbonyl-diimidazole are suspended in 10 ml of toluene at 25° C. The reaction mixture is heated to boiling, then heated to boiling for 2 hours, cooled to room temperature and 2.5 ml of ethanol are added. The reaction mixture is stirred in an ice-cold water bath for an hour. The precipitated solid substance is filtered and dried under an infrared bath to constant weight. Thus 0.3 g (68%) of a white solid substance is obtained. Mp.: 133-137° C.

II 3.3 g (0.083 mole) of 4-{4-[5-iodomethyl-2-oxo-1,3-oxazolidine-3-yl]-phenyl}-morpholine-3-one (rac10c) are stirred in 87 cm$^3$ of dibenzyl amine (16) whereupon 1.73 g (0.0053 moles) of cesium carbonate are added. The reaction mixture is reacted at 80° C. for 35 hours, the cesium carbonate is filtered and the dibenzyl amine is distilled off. The oily residue (7.9 g) is stirred with 40 cm$^3$ of diethyl ether and allowed to crystallize under stirring at 25° C. overnight. The product is filtered, washed with ether and dried. Thus 3.6 g (93.5%) of the crude product melting at 126-128° C. are obtained. The crude product is recrystallized from 105 ml of methanol. 1.7 g (75%) of the white desired product are obtained. Mp.: 146-148° C.

The IR, $^1$H NMR and $^{13}$C NMR data are identical with those of compound 13R.

Example 9

Preparation of the racemic formic acid salt of 4-{4-[(5S)-5-aminomethyl-2-oxo-1,3-oxazolidine-3-yl]-phenyl}-morpholine-3-one of the Formula

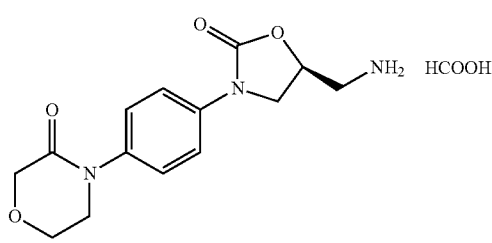

3c 0.30 g (0.64 millimoles) of 4-(4-{5-[(dibenzylamino)-methyl]-2-oxo-1,3-oxazolidine-3-yl}-phenyl)-morpholine-3-one of the Formula 13 (racemic form) is dissolved in a mixture of 12 cm³ of methanol and 0.12 cm³ of formic acid at room temperature. To the solution 0.03 g of a 10% palladium-charcoal catalyst are added and the mixture is hydrogenated in an autoclave under a hydrogen pressure of 10 bar. Hydrogenation is carried out for 44 hours, whereupon the catalyst is filtered off and the filtrate is evaporated to dryness. To the residue 10 cm³ of ethanol are added, the precipitated product is filtered and dried under an infrared lamp to constant weight. Thus 0.12 g (67%) of the white solid title compound is obtained. Mp.: 113-115° C.

Example 10

Preparation of racemic 4-{4-[(5S)-5-aminomethyl-2-oxo-1,3-oxazolidine-3-yl]-phenyl}-morpholine-3-one acetic acid salt (racemic form of the compound of the Formula 3b)

5.15 g (10.90 millimoles) of 4-(4-{(5S)-5-[dibenzylamino-methyl]-2-oxo-1,3-oxazolidine-3-yl}-phenyl)-morpholine-3-one of the Formula 13 (racemic form) are dissolved in 100 ml of glacial acetic acid at room temperature. To the solution 0.5 g of a 10% palladium-charcoal catalyst are added. Hydrogenation is carried out in an autoclave at room temperature under a hydrogen pressure of 10 bar for 24 hours. The reaction mixture is then warmed to 40° C. and the catalyst is filtered off. The filtrate is evaporated to dryness and from the residue four times 50 cm³ of ethanol each are distilled off at a pressure of 75 mbar. To the residue thus obtained 30 cm³ of ethanol are added, the mixture is stirred in a cooling bath for 30 minutes. The precipitated solid substance is filtered off, washed with 25 cm³ of ethanol on the filter and dried under an infrared lamp to constant weight. Thus 3.80 g (99.2%) of the white solid title compound are obtained, HPLC purity 99.7%, mp.: 145-146° C.

Example 11

Preparation of Rivaroxaban (Compound of the Formula 1) from the Compound of the Formula 3b

I 1.9 g (11.7 millimoles) of 5-chloro-thiophen-2-carboxylic acid (15) and 1.9 g (11.7 millimoles) of N,N'-carbonyl-diimidazole are dissolved in 50 ml of dried acetonitrile. The reaction mixture is stirred at 50-55° C. for an hour, then allowed to cool to room temperature. To the solution at this temperature a room temperature solution of 0.78 g (9.3 millimoles) of sodium carbonate and 3.2 g (69.1 millimoles) of 4-{4-[(5S)-5-aminomethyl-2-oxo-1,3-oxazolidine-3-yl]-phenyl}-morpholine-3-one acetate (3b) in 17 ml of water and 10 ml of acetonitrile is added dropwise. The reaction mixture is stirred at 50-55° C. for an hour, then cooled in an ice-cold water-bath and stirred for half an hour. The precipitated solid is filtered off, washed three times with 10 ml of distilled water each and 10 ml of acetone and dried under an infrared lamp to constant weight. Thus 2.33 g (59%) of the title compound are obtained, HPLC purity 99.47%.

The crude product is crystallized from 14 ml of glacial acetic acid to yield 2.04 g (70%) of rivaroxaban, HPLC purity 99.85%. Mp.: 230-231° C.

II

One proceeds as described in Par. I except that as base 1.23 g (9.5 millimoles) of N'N-diisopropyl.-ethylamine are used. The quality of the crude product thus obtained (2.17 g, 55%) is identical with that of the crude product prepared by process I.

Example 12

Preparation of Rivaroxaban (Compound of the Formula 1) from the Compound of the Formula 3a To a mixture of 1.51 g (15 millimoles) of triethyl amine and 15 ml of dichloro methane 0.81 g (7.5 millimoles) of chloro ethyl formiate are added dropwise at room temperature. To the reaction mixture a mixture of 0.8 g (5 millimoles) of 5-chloro-thiophen-2-carboxylic acid (15) and 5 ml of dichloro methane is added dropwise. The reaction mixture is stirred at room temperature for an hour whereupon 1.64 g (5 millimoles) of 4-{4-[(5S)-5-aminomethyl-2-oxo-1,3-oxazolidine-3-yl]-phenyl}-morpholine-3-one hydrochloride (3a) are added. The reaction mixture is stirred for half an hour at room temperature. The triethyl amine hydrochloride salt formed is filtered and the filtrate evaporated to dryness. The residue is suspended in 10 ml of glacial acetic acid, the suspension is heated to boiling and stirred for 10 minutes. The solution is allowed to cool to room temperature, then inoculated with a spatula amount of rivaroxaban (1) crystals and stirred under ice-cooling for 20 minutes. The precipitated white solid product is filtered and dried under an infrared lamp to constant weight. Thus 0.80 g (37%) of the title compound are obtained. Mp.: 230-233° C.

Example 13

Preparation of Rivaroxaban (Compound of the Formula 1) from the Compound of the Formula 3a 0.16 g (1 millimole) of 5-chloro-thiophen-2-carboxylic acid (15) is added to 4 ml of dried acetonitrile. To the suspension 0.13 g (1 millimole) of N,N'-diisopropyl-carbodiimide is added under argon. The reaction mixture is stirred at room temperature for 30 minutes whereupon the solution is added dropwise to a mixture of 0.33 g (1 millimole) of 4-{4-[(5S)-5-aminomethyl-2-oxo-1,3-oxazolidine-3-yl]-phenyl}-morpholine-3-one-hydrochloride (3a) and 0.10 g (1.25 millimoles) of sodium hydrogen carbonate in 4 cm³ of dried acetonitrile at room temperature. The reaction mixture is stirred at 50° C. for 4.5 hours, then heated to the boiling point and stirred at this temperature for 6 hours. The reaction mixture is allowed to cool to room temperature, the solid product is washed twice with 25 cm³ of distilled water each and dried under an infrared lamp to constant weight. Thus 0.24 g (56%) of the title compound is obtained. Mp.: 230-233° C.

Example 14

Preparation of Rivaroxaban (Compound of the Formula 1) from the Compound of the Formula 3a 0.16 g (1 millimole) of 5-chloro-thiophen-2-carboxylic acid (15) and 0.25 g (2.5 millimoles) of triethyl amine are weighed in 8 ml of dried dichloro methane. To the mixture thus obtained 0.16 g (1 millimole) of chloro ethyl formiate are added dropwise at room temperature. The reaction mixture is stirred at room temperature for 30 minutes whereupon the solution obtained is added to a mixture of 0.33 g (1 millimole) of 4-{4-[(5S)-5-aminomethyl-2-oxo-1,3-oxazolidine-3-yl]-phenyl}-morpholine-3-one-hydrochloride (3a) in 4 cm³ of dried dichloro methane. The reaction mixture is allowed to cool to room temperature, the triethyl amine hydrochloride salt formed is filtered off, the filtrate is evaporated to dryness. The residue thus obtained is stirred in a mixture of 2 cm³ of acetone and 3 cm³ of distilled water for 20 minutes. The beige solid obtained is filtered, washed twice with 0.5 cm³ of distilled water each and dried under an infrared lamp to constant weight. Thus 0.10 g (23%) of the title compound is obtained. Mp.: 230-235° C.

Example 15

Preparation of Rivaroxaban (Compound of the Formula 1) from the Compound of the Formula 3a 1.9 g (11.7 millimoles) of 5-chloro-thiophen-2-carboxylic acid (15) and 1.9 g (11.7 millimoles) of N,N'-carbonyl-diimidazole are dissolved in 50 ml of dried acetonitrile. The reaction mixture is stirred at 50-55° C. for an hour whereupon 0.78 g (9.3 millimoles) of sodium carbonate, 3.27 g (10 millimoles) of 4-{4-[(5S)-5-aminomethyl-2-oxo-1,3-oxazolidine-3-yl]-phenyl}-morpholine-3-one hydrochloride and 1 ml of distilled water are added. The reaction mixture is stirred at 50° C. for an hour, cooled in an icecold bath and stirred for a further 0.5 hours. The precipitated solid is filtered, washed three times with 10 ml of water each and 10 ml of acetone and dried under an infrared lamp to constant weight. Thus 3.9 g (77%) of the title compound are obtained. This crude product is recrystallized from 24 ml of glacial acetic acid. Thus 3.34 g (86%) of rivaroxaban are obtained in a HPLC purity of 99.0%. Mp.: 229-230° C.

Example 16

Preparation of Rivaroxaban (Compound of the Formula 1) from the Compound of the Formula 3a Into 8 ml of dried tetrahydrofurane 0.16 g (1 millimole) of 5-chloro-thiophen-2-carboxylic acid (15), 0.16 g (1 millimole) of N,N'-carbonyl-diimidazole, 0.10 g (11.25 millimoles) of sodium hydrogen carbonate and 0.33 g (1 millimole) of 4-{4-[(5S)-5-aminomethyl-2-oxo-1,3-oxazolidine-3-yl]-phenyl}-morpholine-3-one-hydrochloride (3a) are weighed in. The reaction mixture is warmed to 50° C. and stirred at this temperature for 13 hours. The reaction mixture is evaporated to dryness. The residue is stirred in a mixture of 5 ml of acetone, 3 cm³ of toluene and 1 cm³ of distilled water for 20 minutes. The precipitated white solid is filtered, washed with a 1:1 mixture of acetone and distilled water and dried under an infrared lamp to constant weight. Thus 0.32 g (74%) of the title compound are obtained, HPLC purity 98.7%. Mp.: 230-233° C.

Example 17

Preparation of Rivaroxaban (Compound of the Formula 1) from the Compound of the Formula (3b)

I 0.16 g (1 millimole) of 5-chloro-thiophen-2-carboxylic acid (15) and 0.35 g (1 millimole) of 4-{4-[(5S)-5-aminomethyl-2-oxo-1,3-oxazolidine-3-yl]-phenyl}-morpholine-3-one-acetate (3b) are dissolved in 6 ml of N,N'-dimethyl-formamide at room temperature. To the solution 0.078 g (0.93 millimole) of sodium carbonate is added whereupon a 50% solution of 1.35 ml of propyl phosphonic anhydride (T3P) in N,N'-dimethyl formamide is added dropwise. The reaction mixture is warmed to 50-55° C. and stirred at this temperature for 19 hours. To the reaction mixture 20 cm³ of distilled water of a temperature of 2° C. are added and the mixture is stirred in an ice-cold water-bath for an hour. The precipitated solid is filtered, washed three times with 1 ml of distilled water each and 1 ml of acetone and dried under an infrared lamp to constant weight. Thus 0.01 g (23%) of the title compound are obtained.

II

One proceed according to Par. I except that as base 0.106 g (1.05 millimole) of triethyl amine is used. The quality of the product obtained (0.09 g, 21%) is identical with that prepared according to process I.

Example 18

Preparation of 4-{4-[((2S)-3-chloro-2-hydroxypropyl)-amino]-phenyl}-morpholine-3-one of the Formula 9aS 25 g (0.13 mole) of 4-(4-amino-phenyl)-morpholine-3-one (5) are suspended in a mixture of 200 ml of acetonitrile and 40 ml of distilled water under stirring whereupon 0.5 ml (11.93 g, 0.13 mole) of (S)-epichlorohydrine are added. The mixture is warmed to 50-50° C. whereupon the light brown solution is stirred for 6 hours and an additional amount of 10.5 ml of (S)-epichlorohydrine is added. After 6 hours to the mixture 2.62 ml (2.3 g) of (S)-epichlorohydrine (11S) are added four times every 6$^{th}$ hour. After addition of the last portion the mixture is stirred for 3 hours. The acetonitrile is distilled off in vacuo and the water is removed from the two-phase system by azeotropic distillation on adding ethyl acetate. On advancement of the distillation the product precipitates from the mixture as a light beige suspension. The product is crystallized overnight at a temperature of (−15) to (−20)° C., then it is filtered, washed with 0-5° C. ethyl acetate and dried under an infrared lamp to constant weight. Thus 25.81 g (70%) of a light beige product having a melting point of 135-137° C., a chemical purity of 94.9% and a chiral purity (HPLC) of 99.5% are obtained.

The crude product is suspended in 150 ml of hexane, the suspension is warmed and to the hot suspension under stirring 500 ml of acetone are added until dissolution takes place. The mixture is allowed to cool to 25° C. and stirred at 0-2° C. for an hour until crystallization takes place. The mixture is filtered and the product is dried under an infrared lamp. Thus 17.8 g (69%) of the title compound are obtained, mp.: 138-139° C., chemical purity 98.2%, chiral purity (HPLC) 99.5%.

IR (KBr): 3377, 1627, 1604, 1531, 1345, 1126.

$^1$H-NMR (DMSO-$d_6$, 500 MHz): 7.03 (d, J=8.4 Hz, 2H), 6.61 (d, J=8.6 Hz, 2H), 5.68 (t, J=5.8 Hz, 1H), 5.32 (d, J=5.1 Hz, 1H), 4.13 (s, 2H), 3.92 (m, 2H), 3.85 (m, 1H), 3.68 (m, 1H), 3.60 (m, 3H), 3.18 (m, 1H), 3.06 (m, 1H).

$^{13}$C-NMR (DMSO-$d_6$, 125 MHz): 165.91, 147.44, 130.56, 126.63, 112.09, 68.94, 67.89, 63.71, 49.74, 48.10, 46.67.

Elementary analysis for the Formula $C_{13}H_{17}ClN_2O_3$ (M: 284.75): C, 54.84%; H, 6.02%; Cl, 12.45%; N, 9.84%. Found: C, 54.87%; H, 6.15%; Cl, 12.35; N, 9.88%.

Rotation: $[\alpha]^{20}_D$=+2.0° (588 nm/20° C.; c=0.1 g/10 ml DMSO)

Example 19

Preparation of 4-{4-[(5S)-5-chloromethyl-2-oxo-1,3-oxazolidine-3-yl]-phenyl}-morpholine-3-one of the Formula 10aS 21.2 g (0.07 mole) of 4-{4-[((2S)-3-chloro-2-hydroxypropyl)-amino]-phenyl}-morpholine-3-one of the Formula (9aS) are suspended in a mixture of 190 cm$^3$ of toluene and 22.3 cm$^3$ of 1-methyl-2-pyrrolidone under stirring whereupon 15.09 g (0.099 mole) of CDI are added. The mixture is stirred at 80-82° C. temperature for 20 minutes, then allowed to cool to 60° C., 43 ml of ethanol are added dropwise, the mixture is allowed to cool gradually to 25° C. whereby the product begins to precipitate. The mixture is stirred at this temperature for 50 hours, whereupon the mixture is evaporated to a half of its volume and crystallized at a temperature between (−15) and (−20° C. overnight. The product is filtered, washed with 0-5° C. acetone and dried under an infrared lamp. Thus 17.1 g (74%) of the title compound are obtained, mp.: 148-150° C., chemical purity 99.5%, chiral purity (HPLC) 99.76%.

IR (KBr): 1743, 1660, 1521, 1313, 1229, 1122.

$^1$H-NMR (DMSO-$d_6$, 500 MHz): 7.59 (d, J=8.8 Hz, 2H), 7.41 (d, J=8.8 Hz, 2H), 5.02 (m, 1H), 4.22 (m, 1H), 4.19 (s, 2H), 4.01 (m, 1H), 3.97 (m, 2H), 3.95 (m, 1H), 3.85 (m, 1H), 3.72 (m, 2H).

$^{13}$C-NMR (DMSO-$d_6$, 125 MHz): 166.10, 153.94, 137.31, 136.37, 126.12, 118.46, 71.27, 67.87, 63.61, 49.14, 47.54, 46.31.

Elementary analysis for the Formula $C_{14}H_{15}ClN_2O_4$ (M: 310.74): C, 54.11%; H, 4.87%; Cl, 11.41%; N, 9.02%. Found: C, 54.01%; H, 4.89%; Cl, 11.37; N, 9.05%.

Rotation: $[\alpha]^{20}_D$=+52.26° (588 nm/20° C.; c=0.1 g/10 ml DMSO)

Example 20

Preparation of 4-{4-[(5S)-5-iodomethyl-2-oxo-1,3-oxazolidine-3-yl]-phenyl}-morpholine-3-one of the Formula 10cS 117 g (0.05 mole) of 4-{4-[(5S)-5-chloromethyl-2-oxo-1,3-oxazolidine-3-yl]-phenyl}-morpholine-3-one (10aS) are stirred in 340 ml of acetonitrile whereupon 122.65 g (0.082 mole) of sodium iodide are added. The reaction mixture is heated to boiling for 15 hours, a further amount of 41.3 g (0.28 mole) of sodium iodide are added. The reaction mixture is heated to boiling for 15 hours, an additional amount of 20.65 g (0.14 mole) of sodium iodide are added. The reaction mixture is heated to boiling for 7 hours, filtered, the acetonitrile is distilled off and to the yellow crystalline residue 200 ml of dichloro methane and 100 ml of water are added under stirring. The phases are separated and the aqueous layer is washed twice with 100 ml of dichloro methane each. The united organic phases are washed three times with 100 ml of water each, dried over magnesium sulfate and evaporated. The yellow substance obtained is stirred in 130 ml of water overnight. The almost white suspension is filtered, washed with water and dried under an infrared lamp. Thus 21.2 g (96%) of the title compound are obtained. Mp.: 158-161° C., chemical purity (HPLC) 95.4%, chiral purity 99.4%

IR (KBr): 1738, 1659, 1518, 1312, 1231, 1121.

$^1$H-NMR (DMSO-$d_6$, 500 MHz): 7.58 (d, J=9.0 Hz, 2H), 7.41 (d, J=8.8 Hz, 2H), 4.73 (m, 1H), 4.21 (m, 1H), 4.19 (s, 2H), 3.97 (m, 2H), 3.72 (m, 2H), 3.68 (m, 1H), 3.62 (dd, $J_1$=5.1 Hz, $J_2$=10.8 Hz, 1H), 3.57 (dd, $J_1$=4.6 Hz, $J_2$=10.8 Hz, 1H).

$^{13}$C-NMR (DMSO-$d_6$, 125 MHz): 166.09, 153.81, 137.31, 136.38, 126.11, 118.52, 70.94, 67.87, 63.61, 50.56, 49.15, 9.92.

Elementary analysis for the Formula $C_{14}H_{15}IN_2O4$ (M: 402.19): C, 41.81%; H, 3.76%; N, 6.97%. Found: C, 42.2%; H, 3.75%; N, 7.09%

Rotation: $[\alpha]^{20}_D$=+52.74° (588 nm/20° C.; c=0.1 g/10 ml DMSO)

Example 21

Preparation of 4-(4-{(5R)-5-(dibenzylaminomethyl]-2-oxo-1.3-oxazolidine-3-yl}-phenyl)-morpholine-3-one of the Formula 13R 20.0 g (0.05 mole) of 4-{4-[(5S)-5-iodomethyl-2-oxo-1,3-oxazolidine-3-yl]-phenyl}-morpholine-3-one (10cS) are stirred in 533 ml of dibenzyl amine (12) whereupon 10.33 g (0.03 mole) of cesium carbonate are added. The reaction is performed at 80° C. for 35 hours. The cesium carbonate is filtered off and the dibenzyl amine is distilled off at 140° C. and under a pressure of 0.2 bar. The brown oily residue (55.65 g) is taken up in 150 ml of diethyl ether and allowed to crystallize under stirring at 25° C. overnight. The light beige substance is filtered, washed with diethyl ether and dried. Thus 20.15 g (86%) of the title compound are obtained. Mp.: 128-133° C., chemical purity 85.5%, chiral purity (HPLC) 97.5%.

The crude product is recrystallized from 260 ml of ethanol, filtered and dried under an infrared lamp. Thus 17.97 g (87%) of the purified product are obtained, mp. 153-155° C., chemical purity 99.9% and chiral purity (HPLC) 99.9%.

IR (KBr): 1733, 1653, 1521, 1415, 1128.

$^1$H-NMR (DMSO-$d_6$, 400 MHz): 7.48 (d, J=9.1 Hz, 2H), 7.39 (d, J=9.1 Hz, 2H), 7.36 (m, 4H), 7.32 (m, 4H), 7.24 (m, 2H), 4.83 (m, 1H), 4.20 (s, 2H), 4.03 (m, 1H), 3.97 (m, 2H), 3.72 (m, 2H), 3.68 (d, 2H), 3.65 (d, J=13.8 Hz, 2H), 3.57 (m, 1H), 2.80 (m, 1H), 2.74 (m, 1H).

$^{13}$C-NMR (DMSO-$d_6$, 100 MHz): 166.11, 154.32, 139.00, 137.18, 136.64, 128.88, 128.41, 127.20, 126.03, 118.46, 71.27, 67.89, 63.63, 58.32, 55.92, 49.18, 48.19.

Elementary analysis for the Formula $C_{28}H_{29}N_3O_4$ (M: 471.56): C, 71.32%; H, 6.20%; N, 8.91%. Found: C, 70.86%; H, 6.28%; N, 8.92%.

Rotation: $[\alpha]^{20}_D$=+19.32° (588 nm/20° C.; c=0.1 g/10 ml DMSO)

Example 22

Preparation of 4-{4-[(5R)-aminomethyl-2-oxo-1,3-oxazolidine-3-yl]-phenyl}-morpholine-3-one-acetate salt of the Formula 3bR 17.48 g (0.037 mole) of 4-(4-{(5R)-5-(dibenzylaminomethyl]-2-oxo-1,3-oxazolidine-3-yl}-phenyl)-morpholine-3-one of the Formula 13R are dissolved in 190 cm³ of glacial acetic acid at room temperature. To the solution 11.72 g of a 10% palladium-charcoal catalyst are added. Hydrogenation is carried out in an autoclave under a hydrogen pressure of 10 bar at room temperature for 24 hours. The hydrogenation having been completed the catalyst is filtered off, the filtrate is evaporated to dryness and from the residue three times 100 cm³ of ethanol each are distilled off under a pressure of 75 mbar. The white suspension obtained is filtered, the wet filter-cake is stirred in 100 cm³ of ethanol by using a 0-5° C. cooling bath for 30 minutes. The snow-white product is filtered, washed with 30 ml of 0-5° C. ethanol on the filter and dried under an infrared lamp to constant weight. Thus 11.97 g (92%) of a white product are obtained, HPLC purity 99.91%, enantiomeric purity 99.9%, mp.: 142-152° C.

The IR, $^1$H NMR and $^{13}$C NMR spectral characteristics of the product are identical with those of compound 3b.

Elementary analysis for the Formula $C_{16}H_{21}N_3O_6$ (M: 351.36): C, 54.7%; H, 6.02%; N, 11.96%. Found: C, 54.27%; H, 6.11%; N, 11.8%

Rotation: $[\alpha]^{20}_D$=+28.77° (588 nm/20° C.; c=0.1 g/10 ml DMSO)

Example 23

Preparation of 5-chloro-N-({(5R)-2-oxo-3-(4-(3-oxo-morpholine-4-yl)-phenyl]-1,3-oxazolidine-5-yl}-methyl-thiophen-2-carboxamide of the Formula 1R (rivaroxaban enantiomer)

A solution of 3.7 g (0.035 mole) of sodium carbonate in 51 ml of water is cooled to 10° C. under stirring whereupon 10.0 g (0.0028 mole) of 4-{4-[(5R)-5-aminomethyl-2-oxo-1,3-oxazolidine-3-yl]-phenyl}-morpholine-3-one-acetate (3bR), 3 cm³ of water and 23 cm³ of acetone are added. The solution is filtered, whereupon at a temperature between 8° C. and 12° C. 16.6 cm³ of a toluene solution of 5-chloro-thiophen-2-carboxylic acid chloride of a concentration of 36.1 g/100 ml are added (corresponding to 5.97 g, 0.033 mole of 5-chloro-thiophen-2-carboxylic acid chloride of the Formula 4). The reaction mixture is warmed to 50° C., whereupon 25 cm³ of acetone are added and the mixture is stirred for a further period of 30 minutes at 50-53° C. The reaction mixture is cooled to 25° C., the precipitated product is filtered, washed three times with 20 ml of acetone each, three times with 20 cm³ of water each and again twice with 20 ml of acetone each. Thus 11.98 g (97%) of the crude product are obtained (mp.: 231-234° C.) which is recrystallized from a 6.2-fold amount of glacial acetic acid. Thus 20.7 g (93%) of the end product are obtained, HPLC purity 99.93%, enantiomer purity 99.9% mp.: 231-234° C.

Elementary analysis for the Formula $C_{19}H_{18}ClN_3O_5S$ (M: 435.89): C, 52.36%; H, 4.16%; Cl, 8.13%; N, 9.64%; S, 7.36%. Found: C, 52.08%; H, 4.29%; Cl, 8.17%; N, 9.37%; S, 7.43%.

Rotation: $[\alpha]^{20}_D$=+41.02° (588 nm/20° C.; c=0.1 g/10 ml DMSO)

Example 24

Preparation of 4-{4-[((2R)-3-chloro-2-hydroxypropyl)-amino]-phenyl}-morpholine-3-one of the Formula 9a 10.4 g (0.0544 mole) of 4-(4-aminophenyl)-morpholine-3-one (5) are suspended in a mixture of 84 ml of acetonitrile and 17 ml of distilled water under stirring whereupon 4.4 ml (5.0 g, 0.054 mole) of (R)-epichlorohydrine (11) are added. The reaction mixture is warmed to 50-52° C., the light brown solution is stirred for 6 hours, whereupon a further 4.4 ml of (R)-epichlorohydrine are added. After 6 hours in intervals of 6 hours four times 1.1 ml (1.25 g, 00.0135 mole) of (R)-epichlorohydrine are added. After introduction of the last portion the reaction is continued for a further period of 3 hours. The mixture is warmed to 60° C. and stirred at this temperature for a further 3 hours. The acetonitrile is distilled off in vacuo, to the two-phase residue ethyl acetate is added and azeotopic distillation is carried out. On advancement of the distillation the product precipitates in the form of a light yellow suspension. Crystallization is carried out at a temperature between (−15) and (−20)° C. overnight. The product is filtered, washed with 0-5° C. ethyl acetate and dried under an infrared lamp to constant weight. Thus 10.3 g (67% (of the desired crude product are obtained, mp.: 132-134° C., chemical purity 95.1%, chiral purity (HPLC) 98.2%.

The crude product is suspended in 35 ml of hexane, the suspension is warmed and to the hot suspension 169 ml of acetone are added dropwise under stirring until the product is dissolved. The mixture is allowed to cool to 25° C. and crystallization is performed at 0-2° C. under stirring for an hour. The product is filtered and dried under an infrared lamp to constant weight. Thus 8.16 g (82%) of the title compound are obtained, mp.: 137-139° C., chemical purity 98%, chiral purity (HPLC) 98.2%.

The IR, $^1$H NMR and $^{13}$C NMR spectral characteristically data of the product are identical with those of the compound 9aS.

Elementary analysis for the Formula $C_{13}H_{17}ClN_2O_3$ (M: 284.75): C, 54.84%; H, 6.02%; Cl, 12.45%; N, 9.84%. Found: C, 54.77%; H, 6.09%; Cl, 12.50; N, 9.87%

Rotation: $[\alpha]^{20}_D$=−2.5° (588 nm/20° C.; c=0.1 g/10 ml DMSO)

Example 25

Preparation of 4-{4-[(5R)-5-chloromethyl-2-oxo-1, 3-oxazolidine-3-yl]-phenyl}-morpholine-3-one of the Formula 10a 7.9 g (0.028 mole) of 4-{4-[((2R)-3-chloro-2-hydroxypropyl)-amino]-phenyl}-morpholine-3-one of the Formula (9a) are suspended in the mixture of 71 ml of toluene and 12 ml of 1-methyl-2-pyrrolidone under stirring whereupon 5.6 g (0.035 mole) of CDI are added. The mixture is reacted at 80-82° C. for 20 minutes and then heated to boiling for an hour. The mixture is allowed to cool back to 60° C. and 15 ml of ethanol are added dropwise. The mixture is cooled gradually to 25° C. whereby the product starts to precipitate from the mixture. The mixture is stirred at this temperature for 50 hours, whereupon it is evaporated to half of its volume. Crystallization is allowed to take place at a temperature between −15° C. and −20° C. C overnight. The product is filtered, washed with 0-5° C. acetone and dried under an infrared lamp to constant weight. Thus 6.9 g (80%) of the title compound are obtained, mp.: 143-146° C., chemical purity 94.6%, chiral purity (HPLC) 99.59%.

The IR, 1H NMR and 13C NMR data of the product are identical with those of compound 10aS.

Elementary analysis for the Formula $C_{14}H_{15}ClN_2O_4$ (M: 310.74): C, 54.11%; H, 4.87%; Cl, 11.41%; N, 9.02%. Found: C, 54.17%; H, 5.05%; Cl, 11.13%; N, 9.39%.

Rotation: $[\alpha]^{20}_D = -53.49°$ (588 nm/20° C.; c=0.1 g/10 ml DMSO)

Example 26

Preparation of 4-{4-[(5R)-5-iodomethyl-2-oxo-1,3-oxazolidine-3-yl]-phenyl}-morpholine-3-one of the Formula 10c 6.5 g (0.02 mole) of 4-{4-[(5R)-5-chloromethyl-2-oxo-1,3-oxazolidine-3-yl]-phenyl}-morpholine-3-one (10) (are stirred in 130 ml of acetonitrile whereupon 46.89 g (0.31 mole) of sodium iodide are added. The reaction mixture is heated to boiling for 15 hours whereupon 15.79 g (0.11 mole) of sodium iodide are added. The reaction mixture is stirred for a further period of 15 hours, an additional 7.89 g (0.053 mol) (of sodium iodide are added and the mixture is heated to boiling for 7 hours. The mixture is filtered, the acetonitrile is distilled off and to the yellow crystalline residue 100 ml of dichloro methane and 200 ml of water are added under stirring. The phases are separated, the aqueous layer is extracted three times with 30 ml of dichloro methane each. The united organic phases are washed three times with 70 ml of water each, dried over magnesium sulfate and evaporated. The yellow crystalline substance obtained is stirred in 60 ml of water overnight. The nearly white suspension is filtered, washed three times with 20 ml of water each and dried under an infrared lamp to constant weight. Thus 8.0 g (95.2%) of the title compound are obtained, mp. 154-157° C. Chemical purity 95.87%, chiral purity 99.7% (HPLC).

The $^1$H NMR and $^{13}$C NMR spectral characteristics of the product are identical with those of the compound 10cS.

Elementary analysis for the Formula $C_{14}H_{15}IN_2O_4$ (M: 402.19): C, 41.81%; H, 3.76%; N, 6.97%. Found: C, 42.04%; H, 3.84%; N, 7.17%.

Rotation: $[\alpha]^{20}_D = -53.55°$ (588 nm/20° C.; c=0.1 g/10 ml DMSO)

Example 27

Preparation of 4-(4-{(5S)-5-(dibenzylamino-methyl]-2-oxo-1,3-oxazolidine-3-yl}-phenyl)-morpholine-3-one of the Formula 13

7.0 g (0.017 mole) of 4-{4-[(5R)-5-iodomethyl-2-oxo-1,3-oxazolidine-3-yl]-phenyl}-morpholine-3-one (10c) are stirred in 187 ml of dibenzyl amine (12) whereupon 3.62 g (0.011 mole) of cesium carbonate are added and the reaction is continued at 80° C. for 35 hours. The cesium carbonate is filtered off and the dibenzyl amine is distilled off at 140° C. under a pressure of 0.2 mbar. The brown oily residue is crystallized under stirring with 70 ml of diethyl ether overnight. The light beige substance is filtered, washed twice with 30 ml of ether each and dried. Thus 7.78 g (94.8%) of the title compound are obtained, mp.: 140-145° C., chemical purity 90.3%, chiral purity (HPLC) 98.5%.

The crude product (7.5 g) is recrystallized from 115 ml of ethanol, filtered, and dried under an infrared lamp to constant weight. Yield 6.2 g (82.7%), mp. 154-156° C. chemical purity 99.4%, chiral purity (HPLC) 99.9%.

The IR, $^1$H NMR and $^{13}$C NMR spectral characteristics of the product are identical with those of the compound 13R.

Elementary analysis for the Formula $C_{28}H_{29}N_3O_4$ (M: 471.56): C, 71.32%; H, 6.20%; N, 8.91%. Found: C, 71.59%; H, 6.28%; N, 8.91%

Rotation: $[\alpha]^{20}_D = -20.02°$ (588 nm/20° C.; c=0.1 g/10 ml DMSO)

Example 28

Preparation of Rivaroxaban of the Formula 1

A solution of 1.11 g (0.01 mole) of sodium carbonate in 16.5 ml of water is cooled to 10° C. under stirring whereupon 3.0 g (0.0085 mole) of 4-{4-[(5S)-5-aminomethyl-2-oxo-1,3-oxazolidine-3-yl]-phenyl}-morpholine-3-one-acetate (3b), 0.9 ml of distilled water and 6.9 ml of acetone are added. To the reaction mixture at 8-12° C. 5 ml of a 36.1% toluene solution of 5-chloro-thiophen-2-carboxylic acid-chloride (4) are added. The reaction mixture is warmed to 50° C., 7.5 ml of acetone are added and the mixture is stirred at 50-55° C. for a further period of 30 minutes. The reaction mixture is cooled to 25° C., the precipitated product is filtered, washed three times with 15 ml of acetone each, three times with 15 ml of water each and again with three times with 15 ml of acetone each and dried under an infrared lamp to constant weight. Thus 3.4 g (91.4%) of a crude product are obtained, HPLC purity 99.61%, mp.: 229-232° C.

The crude product is recrystallized from 21 ml of glacial acetic acid. 2.99 g (88%) of the white title compound are obtained, HPLC purity 99.88%, mp. 230-232° C.

Example 29

Preparation of racemic 4-{4-[(3-chloro-2-hydroxy-propyl)-amino]-phenyl}-morpholine-3-one of the Formula rac9a 2.4 g of 4-(4-amino-phenyl)-morpholine-3-on (5) are suspended in a mixture of 424 ml of ethanol and 12 ml of distilled water under stirring whereupon 0.98 ml (1.16 g, 0.013 mole) of racemic epichlorohydrine is added. The mixture is stored at 25° C. for 72 hours whereupon 0.42 ml of racemic epichlorohydrine is added. After 24 hours a further 0.42 ml of racemic epichlorohydrine is added. The reaction is continued for 24 hours the reaction mixture is poured into 145 ml of water and the mixture is extracted with 145 ml of ethyl acetate under stirring. The layers are separated, the aqueous phase is extracted three times with 75 ml of ethyl acetate each, the united organic layers are dried over magnesium sulfate, clarified with activated charcoal and filtered. The filtrate is evaporated until a thick suspension is formed. The mixture is cooled to 25° C., washed with 0-5° C. acetone and dried under an infrared lamp to constant weight. Thus 2.0 g (62%) of the title compound are obtained, mp.: 152-153° C.

The IR, $^1$H NMR and $^{13}$C NMR a data of the product are identical with those of compound 9aS.

Example 30

Preparation of racemic 4-{4-[5-chloromethyl-2-oxo-1,3-oxazolidine-3-yl]-phenyl}-morpholine-3-one of the Formula rac10a 1.66 g (0.0058 mole) of racemic 4-{4-[(3-chloro-2-hydroxypropyl)-amino]-phenyl}-morpholine-3-one of the Formula (rac9a) are suspended in a mixture of 16.5 ml of toluene and 2.5 ml of 1-methyl-2-pyrrolidone under stirring whereupon 11.15 g (0.007 mole) of CDI are added. The mixture is reacted at 80-82° C. for 20 minutes whereupon it is heated to boiling for an hour. The mixture is allowed to cool to 60° C. and 3 ml of ethanol are added dropwise. The mixture is gradually cooled to 25° C. The product begins to precipitate. The mixture is stirred at this temperature for 48 hours, filtered, washed with 0-5° C. acetone and dried under an infrared lamp to constant weight—Thus 1.69 g (94% (of the title compound are obtained, mp.: 188-191° C.

The IR, $^1$H NMR and $^{13}$C NMR a data of the product are identical with those of compound 10aS.

Example 31

Preparation of racemic 4-{4-[5-iodomethyl-2-oxo-1,3-oxazolidine-3-yl]-phenyl}-morpholine-3-one of the Formula rac10c 4.0 g (0.013 mole) of 4-{4-[(5-chloromethyl-2-oxo-1,3-oxazolidine-3-yl]-phenyl}-morpholine-3-one (rac10a) are stirred in 100 ml of acetonitrile whereupon 28.92 g (0.087 mole) of sodium iodide are added. The reaction mixture is heated to boiling for 15 hours, a further 13.02 g (0.087 mole) of sodium iodide are added and the reaction mixture is heated to boiling for an additional period of 15 hours. After filtration the acetonitrile is filtered off and to the yellow crystalline residue 50 ml of dichloro methane and 25 ml of water are added under stirring. The layers are separated and the aqueous phase is extracted twice with 25 ml of dichloro methane each. The united organic layers are washed three times with 25 ml of water each, dried over magnesium sulfate and dried. The yellow crystalline substance thus obtained is stirred in 30 ml of water overnight. The nearly white suspension is filtered, washed with water and dried under an infrared lamp to constant weight. Thus 4.18 g (80%) g of the title compound are obtained. Mp.: 167-168° C.

The IR, $^1$H NMR and $^{13}$C NMR a data of the product are identical with those of compound 10cS.

Example 32

Preparation of 4-{4-[5-(aminomethyl)-2-oxo-1,3-oxazolidine-3-yl]-phenyl}-morpholine-3-one base racemate of the Formula 12

0.5 g (0.0015 mole) of racemic 4-{4-[5-aminomethyl-2-oxo-1,3-oxazolidine-3-yl]-phenyl}-morpholine-3-one acetate salt (rac3b) are suspended in 10 ml of distilled water under stirring. The mixture is cooled to 5-10° C. and the pH is adjusted to 10-11 by adding a 1 M sodium hydroxide solution. The reaction mixture is stirred at 25° C. for 20 hours, 20 ml of dichloro methane are added. The layers are separated after stirring for 30 minutes. The aqueous phase is extracted three times with 10 ml of dichloro methane each. The united organic layers are evaporated, Thus 0.33 g (80%) of the title base are obtained. HPLC purity 99.12%. Mp.: 147-149° C.

Elementary analysis for the Formula $C_{14}H_{17}N_3O_4$ Elementary analysis for the Formula (M: 291.31): C, 57.72%; H, 5.88%; N, 14.42%. Found: C, 57.35%; H, 6.04%; N, 14.32%.

Example 33

Preparation of Racemic Rivaroxaban of the Formula rac1

A solution of 0.64 g (0.006 mole) of sodium carbonate in 9 ml of water is cooled to 10° C. under stirring whereupon 1.8 g (0.005 mole) of 4-{4-[5-aminomethyl-2-oxo-1,3-oxazolidine-3-yl]-phenyl}-morpholine-3-one acetate (rac3b) 0.6 ml of water and 1.8 ml of acetone are added. The solution is filtered and at a temperature of 8-12° C. 3 ml of a toluene solution of 5-chloro-thiophen-2-carboxylic acid chloride (compound of the Formula 4) having a concentration of 36.1 g/100 ml are added. (this corresponds to 1.07 g, 0.059 mole) of 5-chloro-thiophen-2-carboxylic acid chloride. The reaction mixture is warmed to 50° C., whereupon 5 ml of acetone are added and the mixture is stirred at 50-53° C. for a further period of 30 minutes. The reaction mixture is cooled to 25° C. The precipitated product is filtered, washed three times with 5 ml of acetone each, three times with 5 ml of water each and again twice with 55 ml of acetone each. Thus 1.75 g (83%) of the title compound are obtained. Mp.: 229-231° C. The product is recrystallized from a 6.2-fold amount of glacial acetic acid. Thus 1.50 g (86%) of the title compound are obtained. Mp.: 230-233° C.

What we claim is:

1. A process for preparing 5-chloro-N-([(5S)-2-oxo-3-[4-(3-oxo-morpholine-4-yl)-phenyl]-1.3-oxazolidine-5-yl)-methyl)-thiophen-2 carboxamide (rivaroxaban) pharmaceutical active ingredient of Formula I

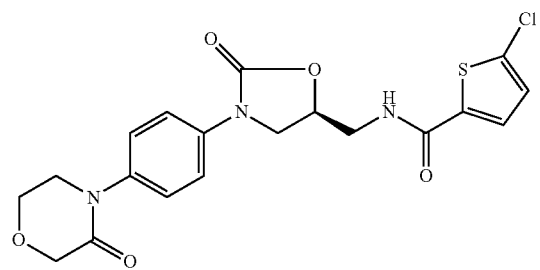

1 which comprises a subjecting 4-(4-((5S(-5-aminomethyl-2-oxo-1,3-oxazolidine-3-yl(-phenyl(-morpholine-3-one of Formula 12

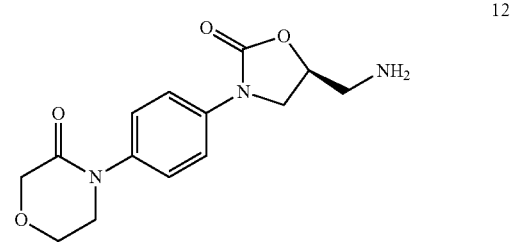 [SMILES: NC[C@H]1CN(c2ccc(N3CCOCC3=O)cc2)C(=O)O1]

12 or a racemate thereof or
a S-enantiomeric salt of Formula 3

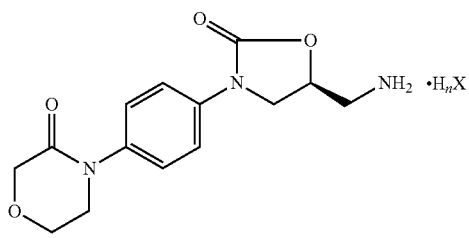

or a racemate thereof
wherein $H_nX$ stands for mono or polyvalent organic or inorganic acid, wherein n represents 1, 2 or 3 and X is an acid residue ion,
if a racemic starting material is used, to resolution,
thereafter reacting with 5-chloro-thiophen-2-carboxylic acid of Formula 15

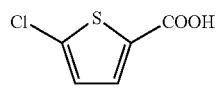

in the presence of a coupling agent; or
b) in the first step subjecting an S-enantiomeric compound of the general Formula

14

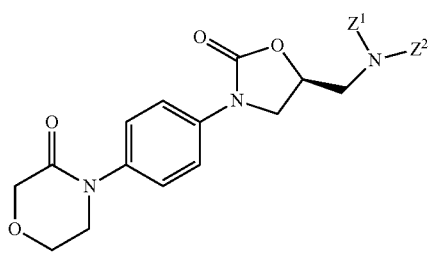

or a racemate thereof (wherein $Z^1$ and $Z^2$ stand for hydrogen or a protecting group with the proviso that at least $Z^1$ is other than hydrogen), if a racemic starting material is used, to resolution and thereafter removing the protecting group(s) and isolating the S-enantiomer base of the Formula 12 thus obtained or a racemate thereof or optionally a salt of same,
in the second step subjecting the product obtained, if a racemic starting material is used, to resolution and thereafter reacting with 5-chloro-thiophen-2-carboxylic acid of the Formula 15
in the presence of a coupling agent; or
c) in the first step subjecting an R-enantiomeric compound of the general Formula

20

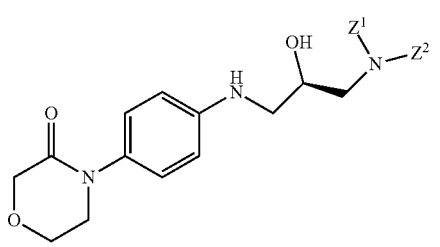

or a racemate thereof, ((wherein $Z^1$ and $Z^2$ are as stated above), if a racemic starting material is used, to resolution, and thereafter reacting with an agent capable of introducing a carbonyl group,
in the second step subjecting the S-enantiomer compound of the general Formula 14 or a racemate thereof obtained (wherein $Z^1$ and $Z^2$ are as stated above), if racemic starting material is used, to resolution, removing the protecting groups(s) and thereafter isolating the S-enantiomer base of the Formula 12 thus obtained or the racemate or optionally a salt thereof,
In the third step subjecting the product obtained, if a racemic starting material is used, to resolution and thereafter reacting with 5-chloro-thiophen-2-carboxylic acid of the Formula 15 in the presence of a coupling agent; or
d) in the first step subjecting a R-enantiomer compound of the general Formula 19

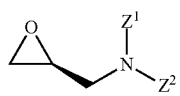

or a racemate thereof (wherein $Z^1$ and $Z^2$ are as stated above), if a racemic starting material is used, to resolution and thereafter reacting with the 4-(4-amino-phenyl)-morpholine-3-one of the Formula 5

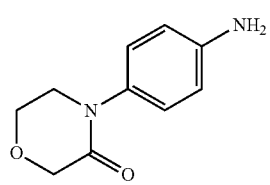

in the second step subjecting the R-enantioner compound of the Formula 20 thus obtained (wherein $Z^1$ and $Z^2$ are as stated above/or the racemate thereof, if a racemic starting material is used, to resolution and thereafter reacting with an agent capable of introducing a carbonyl group,
in the third step subjecting the S-enantioner compound of the Formula 14 obtained (wherein $Z^1$ and $Z^2$ are as stated above) or the racemate thereof, if a racemic starting material is used, to resolution, thereafter removing the protecting groups(s) and isolating the S-enantiomer base of the Formula 12 thus obtained or the racemate or optionally a salt thereof,
in the fourth step subjecting the product thus obtained, if a racemic starting material is used, to resolution and reacting with 5-chloro-thiophen-2-carboxylic acid of the Formula 15 in the presence of a coupling agent; or
e) in the first step reacting the S-enantiomer compound of the Formula 11

or the racemate thereof with a compound of the general Formula $Z^1Z^2NH$ (wherein $Z^1$ and $Z^2$ are as stated above),
in the second step subjecting the R-enantiomer compound of the general Formula 19 or the racemate thereof (wherein $Z^1$ and $Z^2$ are as stated above), if a racemic starting material is used, to resolution and thereafter reacting with 4-(4-amino-phenyl)-morpholine-3-one of the Formula 5, in the third step subjecting the R-enantiomer compound of the general Formula 20 obtained or a racemate thereof (wherein $Z^1$ and $Z^2$ are as stated above), if a racemic starting material is used, to resolution and thereafter reacting with an agent capable of introducing a carbonyl group, in the fourth step subjecting the S-enantiomer compound of the general Formula 14 obtained or a racemate thereof obtained, if a racemic starting material is used, to resolution and thereafter removing the protecting group(s) and isolating the S-enantiomer base of the Formula 12 thus obtained or the racemate thereof or optionally a salt of same, In the fifth step subjecting the compound obtained, if a racemic starting material is used, to resolution and thereafter reacting with 5-chloro-thiophen-2-carboxylic acid of the Formula 15 in the presence of a coupling agent;

Wherein the coupling agent in a) to e) is one or more coupling agents, each of which is selected from the group consisting of chloroethyl formate,
N,N'-diisopropyl-carbodiimide (DIC),
N,N'-dicyclohexyl-carbodiimide (DCC),
tripropyl phosphonic acid anhydride (T3P) and
N,N'-carbonyl-diimidazole (CDI);

with the proviso that if in the compound of the general Formula 3 n represents 1 and X stands for chlorine, then the coupling agent is other than N,N'-carbonyl-diimidazole.

2. The process according to claim 1, wherein n represents 1 and X stands for an acetate ion.

3. Process according to variants b), c), d) and e) of claim 1 wherein in the general Formula 14, $Z^1$ and $Z^2$ stand for benzyl.

4. Process according to variants c), d) and e) of claim 1 wherein in the general Formula 20, $Z^1$ and $Z^2$ stand for benzyl.

5. Process according to variants d) and e) of claim 1 wherein in the general Formula 19, $Z^1$ and $Z^2$ stand for benzyl.

6. Process according to variant e) of claim 1 wherein in the general Formula $Z^1Z^2NH$, $Z^1$ and $Z^2$ stand for benzyl.

7. The process according to claim 1, wherein the reaction of the S-enantiomer base of Formula 12 or the racemate or optionally a salt thereof with the 5-chloro-thiophen-2-carboxylic acid of Formula 15 is carried out optionally in the presence of an organic or inorganic base, in an organic solvent, at 0-110° C.

8. Process according to claim 1 wherein the protecting groups of the S-enantiomer compound of the Formula

13

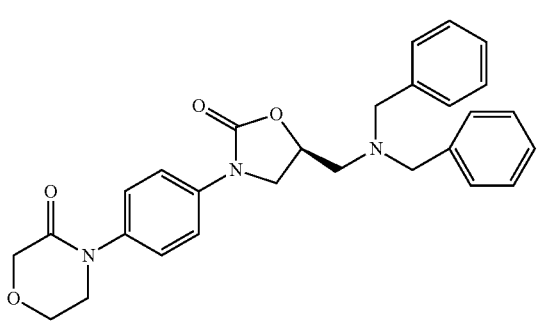

which is the general Formula 14 wherein $Z^1$ and $Z^2$ are each benzyl- or the racemate thereof are removed by reduction and the reduction is carried out in a C1-4 aliphatic alcohol, glacial acetic acid, water or a mixture of said solvents formed with each other or further organic solvents, by catalytic hydrogenation or chemical reduction.

9. Process according to claim 1 wherein in the conversion of a R-enantiomer compound of the general Formula 20 or a racemate thereof into an S-enantiomer compound of the general Formula 14 or a racemate thereof (wherein $Z^1$ and $Z^2$ stand for hydrogen or a protecting group with the proviso that at least Z is other than hydrogen) as agent capable of introduction of a carbonyl group N,N'-carbonyl-diimidazole, phosgene, diphosgene or triphosgene, preferably N,N'-carbonyl-diimidazole is used and the reaction is carried out in a suitable solvent, preferably toluene.

10. Process according to claim 1 wherein the reaction of the R-enantiomer compound of the general Formula 19 or a racemate thereof (wherein $Z^1$ and $Z^2$ stand for hydrogen or a protecting group with the proviso that at least $Z^1$ is other than hydrogen) and the 4-(4-amino-phenyl)-morpholine-3-one of the Formula 5 is carried out preferably in a protic solvent or solvent mixture or in a mixture of a protic solvent and water at 0-150° C. preferably 60-90° C. for a period of 0.5-60 hours preferably 20-40 hours.

11. Process according to claim 1 wherein the reaction of the S-enantiomer compound of the Formula 11 or the racemate thereof and a compound of the general Formula $Z^1Z^2NH$ (wherein $Z^1$ and $Z^2$ stand for hydrogen or a protecting group with the proviso that at least $Z^1$ is other than hydrogen), preferably the N-benzyl-1-phenyl-methaneamine of the Formula

16

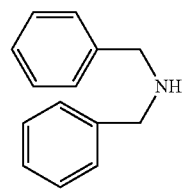

is carried out in the absence or presence of an organic solvent or in water or in a mixture of said solvents, preferably in the presence of an organic or inorganic acid binding agent.

12. The process according to claim 7, wherein the coupling agent is a chloroethyl formate or N,N'-carbonyl-diimidazole (CDI).

13. The process according to claim 7, wherein the reaction is carried out in the presence of an organic or inorganic base.

14. The process according to claim 7, wherein the reaction is carried out in the presence of an organic or inorganic base, which is triethyl amine, diisopropyl ethyl amine, sodium carbonate or sodium hydrogen carbonate.

15. The process according to claim 7, wherein the organic solvent is acetonitrile, dichloro methane, acetone, toluene, tetrahydrofuran or a mixture thereof or a mixture thereof with water.

16. The process according to claim 7, wherein the reaction is carried out at 40-70° C.

17. The process according to claim 1, wherein the reaction is performed in the presence of a single coupling agent.

18. The process according to claim 7, wherein the reaction is performed in the presence of a single coupling agent.

19. The process according to claim 1, wherein the reaction is performed in the presence of a single coupling agent, which is N,N'-carbonyl-diimidazole.

* * * * *